United States Patent [19]
Radosevich et al.

[11] Patent Number: 5,429,949
[45] Date of Patent: Jul. 4, 1995

[54] S-TRIAZINE DEGRADING BACTERIA

[75] Inventors: Mark Radosevich, Newark, Del.; Olli H. Tuovinen; Samuel J. Traina, both of Columbus, Ohio

[73] Assignee: Ohio State Research Foundation, Columbus, Ohio

[21] Appl. No.: 199,065

[22] Filed: Feb. 22, 1994

[51] Int. Cl.$^6$ .............................................. C12N 1/20
[52] U.S. Cl. ............................ 435/252.1; 435/262.5; 210/612
[58] Field of Search .................... 435/252.1, 262.5; 210/612

[56] References Cited

U.S. PATENT DOCUMENTS 4,274,955 6/1981 Zeyer ................................... 210/612
4,745,064 5/1988 Cook ..................................... 435/42
4,859,594 8/1989 Portier ................................. 435/172.1
5,011,599 4/1991 Kearney et al. .

OTHER PUBLICATIONS

Giardina et al., Ann. Microbiol., 27, 127–130, 1977.
Baggi, G., Ann. Microbiol., 39, 203–212, 1989.
El-Dahtory et al., Zbl. Mikrobiol., 139, 375–382, 1984.
Kaufman et al., Residue Rev. (1970) 32, 235–265.
Leeson et al., J. Agric. Food Chem., 41, 1993, pp. 983–987.
Giardi, et al., Agric. Biol. Chem., 49(6), 1985, 1551–1558.
Voinova et al., Meded. Fac. Landbouwwetensch., Rijksuniv. Gent, (1970), 35(2), 836–46.
Cook et al., J. Agric. Food Chem., 1981, 29, pp. 1135–1143.
"Mineralization of the s-Triazine Ring of Atrazine by Stable Bacterial Mixed Cultures", Mandelbaum et al., Applied and Environmental Microbiology, vol. 59, No. 6, Jun. 1993, pp. 1695–1701.
"Microbial Degradation of Simazine", Kaufman et al., J. Ag. Food Chem., vol. 13, No. 3, May–Jun. 1965, pp. 238–242.
"Degradation of Atrazine and its Metabolites", Behki et al., J. Ag. Food Chem., vol. 34, No. 4, Mar. 1986, pp. 746–749.
"Anaerobic Degradation of Cyanuric Acid, Cysteine, and Atrazine by as Facultative Anaerobic Bacterium", Jessee et al., Applied and Environmental Microbiology, vol. 45, No. 1, Jan. 1983, pp. 97–102.
"Biological Treatment Specific for an Industrial Wastewater Containing s-Trazines", Hogrefe et al., Biotechnology and Bioengineering, vol. 27, Sep. 1985, pp. 1291–1295.
"Chemical and Biological Degradation of Primary Metabolites of Atrazine by a Nocardia Strain", Giardi et al., Agric. Biol. Chem., vol. 49, No. 6, 1985, pp. 1551–1558.
"Deethylsimazine: Bacterial Dechlorination, Deamination, and Complete Degradation", Cook et al., J. Agr. Food Chem., vol. 32, No. 3, Feb. 1984, pp. 581–585.
"Metabolism of the Herbicide Atrazine by Rhodococcus Strains", Behki et al., Applied and Environmental Microbiology, vol. 59, No. 6, Jun. 1993, pp. 1955–1959.
Abstract, "Aerobic and Anaerobic Degradation of Atrazine by Surface and Subsurface Microbial Consortia" by Radosevich, et al., ASM, May 1992, p. 317 (C–49).

Primary Examiner—Irene Marx
Attorney, Agent, or Firm—Calfee, Halter & Griswold

[57] ABSTRACT

A pure bacterial culture, designated herein as M91-3, has been isolated which rapidly degrades certain s-triazines, particularly halogenated s-triazines. The M91-3 degrades s-triazines, particularly atrazine, beyond the point of ring cleavage, leading to complete mineralization of the atrazine. The ability of M91-3 to completely degrade atrazine appears to be unique among bacteria. The M91-3 is capable of degrading s-triazine in solution and in presence of soil or sediment. The invention also relates to a method for degrading s-triazines, particularly atrazine.

1 Claim, 17 Drawing Sheets

S-TRIAZINE DEGRADING BACTERIA

FIELD OF THE INVENTION

This invention relates to the discovery and isolation of a novel nongenetically engineered bacteria for degrading s-triazine compounds and to the method for degrading such s-triazines.

BACKGROUND OF THE INVENTION s-Triazines compounds are a family of herbicides which encompass symmetrical triazines, including, for example, atrazine, simazine and cyanazine. Atrazine is an extensively used herbicide for broadleaf weed control among corn and sorghum crops. Approximately 48–50 million acres of farmland under corn production are treated with atrazine annually. The widespread use of atrazine has created environmental concern particularly as a result of the frequent detection of atrazine in surface water, rain water, tile drainage, and ground water, frequently at concentrations exceeding the maximum contaminant level of 3 $\mu g\ l^{-1}$ set by the EPA. Atrazine has been classified as a moderately persistent herbicide, with field dissipation rates ranging from 0.006 to 0.01 $d^{-1}$ with half-lives ranging up to many months in soils. Indeed, residues of the s-triazines and their derivatives have been detected in soils years after application. s-Triazines are now targeted for removal or remediation at sites exceeding maximum contaminant levels.

One method proposed for remediating sites containing s-triazines involves large-scale excavation of the contaminated soil followed by thin spreading of the contaminated soil on fallow agricultural land. This method relies upon a combination of indigenous soil microbial populations to eventually degrade the herbicides thereby reducing herbicide levels in the contaminated soil. Unfortunately, the presence of the herbicide renders the field unsuitable for subsequently planting numerous crops. Moreover, contaminated soils often contain mixtures of pesticides or herbicides, which severly limits the use of the field for a wide variety of subsequent crops. Also, thin-spreading of these contaminated soil can injure crops during subsequent growing seasons. Furthermore, compounds may be present in the contaminated soil which are not licensed for agricultural application and thin-spreading may not, therefore, be a suitable remediation method.

Alternatively, remediation of contaminated sites often involves excavation and incineration of large quantities of soil, which is extremely costly and consumes a large portion of the limited funds available for remediation.

Accordingly, it would be desirable to have an inexpensive, rapid method for degrading s-triazine.

SUMMARY OF THE INVENTION

A pure bacterial culture, designated herein as M91-3, has been isolated which rapidly degrades certain s-triazines, particularly halogenated s-triazines. The M91-3 degrades s-triazines, particularly atrazine, beyond the point of ring cleavage, leading to complete mineralization of the atrazine. The ability of M91-3 to completely degrade atrazine appears to be unique among bacteria. The M91-3 is capable of degrading s-triazine in solution and in presence of soil or sediment. The invention also relates to a method for degrading s-triazines, particularly atrazine.

DETAILED DESCRIPTION OF THE INVENTION

Figure 1A:
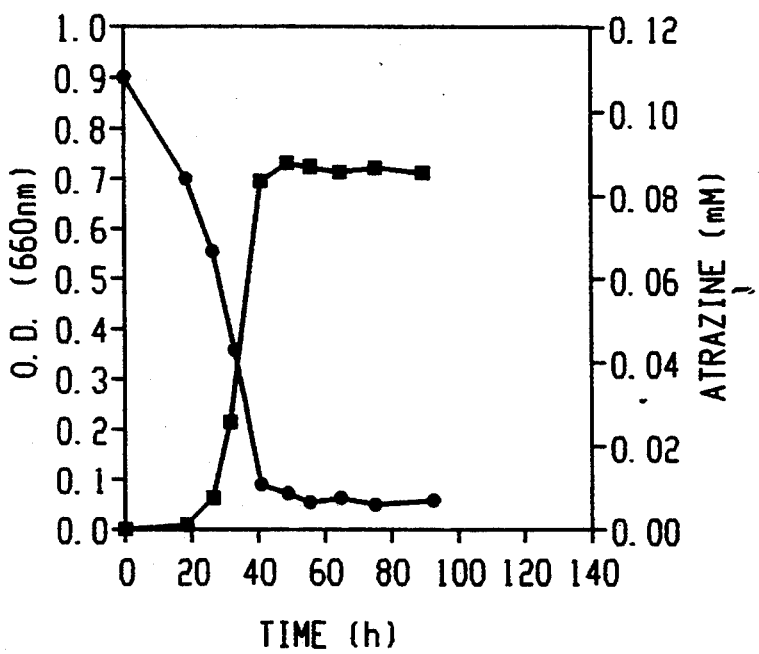
FIG. 1A. is a graph showing M91-3 degradation of atrazine, represented by circles, in media supplemented with glucose.

An s-triazine-degrading bacteria, herein designated as "M91-3" was isolated, and pure culture obtained M91-3 has been deposited with the American Type Culture Collection Accession Number 55551. The M91-3 is a gram-negative, rod-shaped, motile, facultatively anaerobic bacterium that can use nitrate as an electron acceptor. In addition to atrazine, 2-chloro-4-ethylamino-6-isopropylamino-s-triazine, the M91-3 is capable of degrading cyanazine and simazine. M91-3 is capable of using atrazine, simazine, or cyanazine as sole source of carbon and nitrogen under aerobic conditions. M91-3 is capable of using atrazine under aerobic conditions as the sole source of: carbon and electrons, or as the sole source or nitrogen (with glucose as an electron donor and carbon source), or as the sole source of carbon, nitrogen, and electrons. M91-3 also utilized cyanuric acid as the sole source of nitrogen indicating that the M91-3 was capable of cleaving the atrazine ring. This was confirmed in $^{14}CO_2$ evolution experiments with (U-$^{14}$C-ring)-atrazine. M91-3 also degrades atrazine under anaerobic conditions. While the complete degradative pathway of atrazine and other s-triazines, by M91-3 remains unknown, the M91-3 degrades the s-triazines beyond the point of ring cleavage. It is believed that microorganism mediated ring cleavage of s-triazines has never been observed for pure bacterial cultures. M91-3 also degrades s-triazines such as atrazine in the presence of natural sorbents contained in soils or sediments. M91-3 also degrades 2-Chloro-4-amino-6-isopropylamino-s-triazine,2-Chloro-4-ethylamino-6-amino-s-triazine, 2-Chloro-4,6-diamino-s-triazine, 2-Hydroxy-4,6-diamino-s-triazine, and 2-Hydroxy-4-ethylamino-6-isopropylamino-s-triazine and utilizes such compounds as nitrogen sources when provided with glucose as a carbon source.

The primary mechanism for the removal of atrazine from the environment, such as soil or water, is thought to be by degradation by a variety of species of indigenous microorganisms; this is typically a very slow process.

Proposed microbial degradation pathways for s-triazines involve multiple steps executed by different microorganisms. The alkyl groups on the side chains are removed by the cleavage of the carbon-nitrogen bond leaving the nitrogen groups bound to the ring. In a subsequent step, the nitrogen is removed from the ring via deamination. The chlorine is removed via a dehalogenation reaction. The resulting product is a trihydroxy substituted s-triazine, cyanuric acid.- A few microorganisms cleave the cyanuric acid ring yielding $CO_2$ and biuret, which is further degraded through urea to $CO_2$ and $NH_3$. However, until discovery of M91-3, no single organism was capable of degrading atrazine through ring cleavage to biuret, urea, $CO_2$ and $NH_3$.

Classification of M91-3

Attempts were made to classify M91-3 by a variety of means. The API-NFT system of Analytab Products, division of Sherrwood Medical, Plainview N.Y. was employed according to the manufacturers' instructions to classify M91-3 based on bio-chemical tests. The results were negative for: tryptophanase, glucose fermentation, arginine dihydrolase, gelatinase, caprate assimilation, adipate assimilation, citrate assimilation, and phenylacetate assimilation. The results were positive for nitrate reduction, urease, esculin hydrolysis, and b-galactosidase. M91-3 assimilated: glucose; L-arabinose; D-mannose; D-mannitol; N-acetyl-D glucosamine; maltose; D-gluconate; and L-malate. The M91-3 was positive for cytochrome c oxidase. The API-NFT system identified the M91-3 as *Agrobacterium radiobacter.*

Attempts were also made to classify M91-3 on the basis of its fatty-acid profile using a Hewlett Packard Microbial Identification System. With one sample, the fatty acid profile provided a similarity index of 0.49 to Xanthobacter sp. The fatty acid profile identified the following M91-3 components: a twelve carbon chain having a hydroxyl group at the third carbon; a sixteen carbon chain; a seventeen carbon chain; an eighteen carbon chain; a collection of isomers having eighteen carbon chains with 1 double bond; a nineteen carbon fatty acid having a cyclo ring between the eleventh and twelfth carbon; a twenty carbon chain having a trans double bond at the eleventh carbon. A second sample had a similarity index of 0.47 to Xanthobacter sp. and identified the same fatty acids as the first sample, but further identified a sixteen carbon chain with a double bond at the ninth carbon.

A third sample identified only the sixteen, seventeen, and eighteen carbon chains, the nineteen carbon chain with the cyclo ring between the eleventh and twelfth carbon; a collection of isomers having eighteen carbon chains with 1 double bond. The similarity index was 0.370 to Xanthobacter sp.

Two samples of the M91-3 were also subjected to a fatty acid profile by a commercial service, Analytical Services, Inc., Essex Junction Vt. employing the microbial identification system Aerobic database and the Rhizobium database. The highest similarity index, 0.307 was obtained with Bradyrhizobium japonicum. The fatty acid profiles were similar to the profile obtained using the Hewlett Packard Microbial Identification System. The fatty acid profile for one sample identified the following: a twelve carbon chain having a hydroxyl group at the third carbon; a sixteen carbon chain; a seventeen carbon chain; a seventeen carbon chain having a double bond; an eighteen carbon chain; a collection of isomers having eighteen carbon chain and 1 double bond; a nineteen carbon fatty acid having a cyclo ring at the eighth carbon; a nineteen carbon chain having a methyl group at the tenth carbon.

The fatty acid profile for the other sample identified the following: a twelve carbon chain having a hydroxyl group at the third carbon; a sixteen carbon chain; a sixteen carbon chain having a double bond between the seventh and eight carbons; a seventeen carbon chain; an eighteen carbon chain; a collection of isomers having an eighteen carbon chain and one double bond; a nineteen carbon fatty acid having a cyclo ring at the eighth carbon; a nineteen carbon chain having a methyl group at the tenth carbon and a twenty carbon chain with a double bond between the ninth and tenth carbon.

The M91-3 was evaluated for its ability to utilize, that is oxidize, a wide variety of carbon sources contained on the Biolog GN Microplate, available from Biolog Inc., Hayward, Calif. The results are shown in Table I. The closest match was to an Aeromonas media-like bacteria and similar to DNA group 5A with a similarity index of 0.079. A comparison of M91-3 to Agrobacterium Radiobacter and Xanthobacter spp. is presented in Table II.

TABLE I

M91-3 Ability to Utilize Various Sources of Carbon

| | | | | | | | | | | | |
|---|---|---|---|---|---|---|---|---|---|---|---|
| A1 water ** | A2 α-cyclodextrin B | A3 dextrin XX | A4 glycogen XX | A5 tween 40 XX | A6 tween 80 XX | A7 N-acetyl-D-galactros-amine ** | A8 N-acetyl-D-glucosamine XX | A9 adonitol ** | A10 L-arabinose ** | A11 D-grabitol XX* | A12 cellobiose **+ |
| B1 i-erythritol ** | B2 D-fructose XX | B3 L-fucose XX* | B4 D-galactose XX | B5 gentiobiose ** | B6 α-D-glucose XX | B7 m-inositrol XX* | B8 α-lactose ** | B9 α-D-lactose lactulose ** | B10 maltose XX | B11 D-mannitol XX | B12 D-mannose XX |
| C1 D-melibiose ** | C2 β-methyl D-glucoside S+ | C3 psicose XX | C4 D-raffinose XX | C5 L-rhamnose ** | C6 D-sorbitol XX | C7 sucrose XX | C8 D-trehalose XX | C9 furanose XX | C10 xylitol ** | C11 methyl pyruvate XX | C12 mono-methyl succinate XX |
| D1 acetic acid XX | D2 cis-aconitic acid ** | D3 citric acid ** | D4 formic acid XX | D5 D-galactonic acid lactone ** | D6 D-galacturonic acid ** | D7 D-gluconic acid **+ | D8 D-glucosaminic acid ** | D9 D-glucuronic acid ** | D10 α-hydroxy butyric acid XX | D11 β-hydroxy butyric acid XX | D12 γ-hydroxy butyric acid XX* |
| E1 p-hydroxy phenylacetic acid ** | E2 itaconic acid ** | E3 α-keto butyric acid ** | E4 α-keto glutanic acid ** | E5 α-keto valeric acid ** | E6 D,L-lactic acid XX | E7 malonic acid ** | E8 propionic acid XX | E9 quinic acid ** | E10 D-saccharic acid ** | E11 sebacic acid ** | E12 succinic acid ** |
| F1 bromo succinic acid ** | F2 succinamic acid ** | F3 glucuron-amide ** | F4 alaninamide XX | F5 D-alanine ** | F6 L-alanine XX | F7 L-alanyl-glycine XX | F8 L-asparagine XX | F9 L-aspertic acid **+ | F10 L-glutamic acid XX | F11 glycyl-L-aspartic acid XX | F12 glycyl-L-glutamic acid XX |
| G1 L-histidine XX | G2 hydroxy L-proline ** | G3 L-leucine XX | G4 L-ornithine XX | G5 L-phenyl alanine XX* | G6 L-proline XX | G7 L-pyro glutamic acid ** | G8 D-serine **+ | G9 L-serine **+ | G10 L-threonine ** | G11 D,L-carnitine ** | G12 γ-amino butyric acid ** |
| H1 urocanic acid XX | H2 inosine XX | H3 uridine XX | H4 thymidine XX | H5 phenyl ethylamine ** | H6 putrescine ** | H7 2-amino ethanol ** | H8 2,3-butanediol ** | H9 glycerol XX | H10 D,L-α-glycerol phosphate **+ | H11 glucose-1-phosphate ** | H12 glucose-6-phosphate ** |

XX = positive
XX* = positive, "=" greater than" ID choice positive less than 10% of the time
** = negative
**+ = negative, "=" greater than" ID choice positive greater than 90% of time
B = borderline

TABLE II

A comparison of physiological characteristics between M91-3, *Agrobacterium Radiobacter* and *Xanthobacter* spp.

| Characteristic | M91-3 | A. radiobacter | Xanthobacter |
|---|---|---|---|
| Morphology | rod | rod | rod |
| Gram Stain | − | − | −/+ |
| Motility | + | + | − |
| $NO_3$ Reduction | + | some strains | − |
| Tryptophanase | − | ? | ? |
| Glucose fermentation | − | + | − |
| Arginine dihydrolase | − | ? | ? |
| Urease | + | + | − |
| Esculin hydrolysis | + | + | ? |
| Gelatinase | − | − | − |
| B-galactosidase | + | + | ? |
| Glucose | + | + | + |
| Arabinose | + | + | ? |
| Mannose | + | ? | ? |
| Mannitol | + | + | ? |
| N-acetyl-D-glucosamine | + | ? | ? |
| Maltose | + | + | ? |
| D-Gluconate | + | ? | + |
| Caprate | − | ? | ? |
| Adipate | − | ? | ? |
| L-Malate | + | − | + |
| Citrate | − | − | + |
| Phenylacetate | − | − | ? |
| Oxidase | + | + | + |

Source for characteristics of *A. Radiobacter* and *Xanthobacter* was Bergey's Manual
? — indicates that the Information was not found in Bergey's Manual.

s-Triazine

Members of s-triazine herbicide family have symmetrical s-triazine ring structure containing two alkyl substituted amino groups, while the third ring carbon is substituted with functional groups such as, for example, chloro, methoxy, or thiomethoxy moieties.

The chemical structures of the triazine compounds used in this study are shown in Table III. The s-triazines have a symetrical ring stucture; the nitrogen and carbons in the ring are arranged symmetrically. The s-triazines have the following structure:

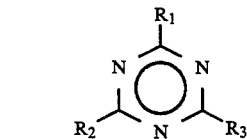

Wherein: R1 is preferably selected from the group of: Cl; OH, $SCH_3$, $OCH_3$, and $NH_2$;
R2 is preferably selected from the group of: OH, $NH_2$, $C_2H_5NH$, $(CH_3)_3CHN$, and $C_3H_7NH$;
R3 is preferably selected from the group of: $C_3H_7NH$, $NHC(CH_3)_2CN$, OH, $NH_2$, and $C_2H_5NH$.

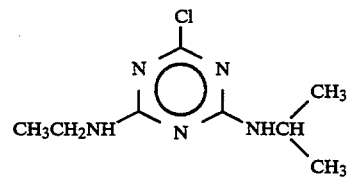

Altrazine

TABLE III

| Functional Group | | | Chemical Name | Common Name | Chem. Abst. Serv. # |
|---|---|---|---|---|---|
| $R_1$ | $R_2$ | $R_3$ | | | |
| Cl | $C_2H_4NH$ | $C_3H_7NH$ | 2-Chloro-4-ethylamino-6-isopropylamino-s-triazine | Atrazine | 1912-24-9 |
| Cl | $C_2H_4NH$ | $C_2H_5NH$ | 2-Chloro-4,6-bis(ethylamino)-s-triazine | Simazine | 122-34-9 |
| Cl | $C_2H_4NH$ | $NHC(CH_3)_2CN$ | 2-Chloro-4-ethylamino-6-aminoisopropyl nitrile s-triazine | Cyanazine | 21725-46-2 |
| Cl | $NH_2$ | $C_3H_7NH$ | 2-Chloro-4-amino-6-isopropylamino-s-triazine | Deethyl-atrazine | 6190-65-4 |
| Cl | $C_2H_5NH$ | $NH_2$ | 2-Chloro-4-ethylamino-6-amino-s-triazine | Deisopropyl-atrazine | 1007-28-9 |
| Cl | $NH_2$ | $NH_2$ | 2-Chloro-4,6-diamino-s-triazine | Deethyl-deisopropyl-atrazine | 3397-62-4 |
| OH | $C_2H_5NH$ | $C_3H_7NH$ | 2-Hydroxy-4-ethylamino-6-isopropylamino-s-triazine | Hydroxy-atrazine | 2163-68-0 |
| OH | $NH_2$ | $C_3H_7NH$ | 2-Hydroxy-4-amino-6-isopropylamino-s-triazine | Deethyl-hydroxy-atrazine | |
| OH | $NH_2$ | $NH_2$ | 2-Hydroxy-4,6-diamino-s-triazine | Ammeline | |
| $NH_2$ | $NH_2$ | $NH_2$ | 2,4,6-Triamino-s-triazine | Melamine | 108-78-1 |
| OH | OH | OH | 2,4,6-Trihydroxy- | Cyanuric acid | 108-80-5 |

TABLE III-continued

Functional groups, chemical formulas, common names, and abbreviations for triazines

| R₁ | Functional Group R₂ | R₃ | Chemical Name | Common Name | Chem. Abst. Serv. # |
|---|---|---|---|---|---|
| | | | s-triazine | | |
| $SCH_3$ | $CH_3H_7NH$ | $C_2H_4NH$ | | Ametryn | 834-12-8 |
| * | * | * | | *Metribuzin | 21087-64-9 |
| $OCH_3$ | $C_3H_7NH$ | $CH_3H_7NH$ | | Prometon | 1610-18-0 |
| $SCH_3$ | $C_3H_7NH$ | $CH_3H_7NH$ | | Prometryn | 7287-19-6 |
| Cl | $C_3H_7NH$ | $CH_3H_7NH$ | | Propazine | 139-40-2 |
| $SCH_3$ | $(CH_3)_3CNH$ | $C_2H_5NH$ | | Terbutryn | 886-50-0 |

*not a symmetrical s-triazine

Atrazine and its metabolites, 2-hydroxy-atrazine; deethylatrazine; deisopropylatrazine; 2-chloro-4,6-diamino-s-triazine; 2-hydroxy-4,6-diamino-s-triazine; and deethyl-2-hydroxy-s-triazine, were obtained from Chemservice, West Chester, PA. The purity of all the s-triazines exceeded 98%. Cyanuric acid, melamine, and bioret were obtained from Aldrich Chemical, Milwaukee, WI and had purities of 98, 99, and 97%, respectively. Urea was obtained from Mallinckrodt.

The M91-3 culture media

The media used in M91-3 cultures was a Basal salts media and had the following composition (per L): $K_2HPO_4$, 0.5 g; $(NH_4)_2SO_4$, 0.5 g; $MgSO_4 \cdot 7H_2O$, 0.5 g; $FeCl_3 \cdot H_2O$, 10 mg; $CaCl_2 \cdot H_2O$, 10 mg; $MnCl_2$, 0.1 mg; $ZnSO_4$, 0.01 mg; pH 6.8. The K-phosphate solution having a pH of 6.8, was prepared separately from the other mineral salts. Atrazine (0.1 mM) was added to the phosphate solution and was placed on a reciprocating shaker overnight. The atrazine solution was sterilized by autoclave. The solution was analyzed by high performance liquid chromatography (HPLC) before and after sterilization to confirm the thermal stability of atrazine. The magnesium sulfate salt solution (100×concentrate) was autoclaved separately and added to each enrichment culture aseptically. The trace element solution, which contains the chloride salts of iron, calcium, and manganese and the sulfate salt of zinc, was prepared separately as a 100×concentrated stock solution and filter sterilized. In some experiments, ammonium was either deleted or replaced by $KNO_3$ (0.77 g $1^{-1}$). In experiments in which only one s-triazine was added to the cultures, then glucose was added as an additional carbon and energy source, at either 1 g $1^{-1}$ or 1.1 mM, as indicated. In experiments in which two s-triazines were added, 2.2 mM, that is 400 mg/l. glucose was added. In experiments in which three s-triazines were added, 3.3 mM glucose was added.

Isolation of M91-3

M91-3 was isolated from agricultural soil that had been subject to a variety of herbicide spills, including atrazine spills.

Four Basal salts media formulations were used and prepared for enrichment cultures under aerobic and anaerobic conditions: media with atrazine and glucose, ammonium-free media with atrazine, glucose and nitrate, ammonium-free media with atrazine and glucose, and ammonium-free media with atrazine. Soil samples from the western Ohio site were added to each of the four types of media.

After successive enrichment, several mixed cultures capable of atrazine degradation were eventually obtained. Fifty-two colonies were isolated and purified from these mixed cultures. These isolates were tested for their ability to degrade atrazine as a source of carbon or nitrogen or both. A single isolate was obtained.

Enrichment cultures of M91-3 exhibiting at least a 25% loss of atrazine were subcultured into identical media and sampling was repeated. Several stable mixed cultures capable of degrading atrazine were obtained. The most effective atrazine-degrading cultures resulted from the ammonium-free media enrichments in which atrazine was provided as the sole source of nitrogen. In an attempt to eliminate satellite growth, the mixed cultures were serially diluted in culture media and the loss of atrazine in these subcultures was again measured over time. The highest dilution still exhibiting degradation of atrazine was diluted in phosphate buffer, and spread plated onto minimal salts agar containing atrazine. The plates were incubated at 25±2° C. Colonies present after one week of incubation were purified by repeated streaking and their ability to degrade atrazine was confirmed in inoculated liquid media. Examination under the microscope revealed the presence of a single cell type; and only a single colony type appeared on the plates confirming that a biologically pure culture of the M91-3 had been obtained.

All incubations were carried out at 25±2° C. unless otherwise noted. Aerobic growth of the M91-3 isolate in media supplemented with glucose as a carbon and energy source and atrazine as the sole source of nitrogen was measured by optical density at 660 nm. Due to the low solubility of atrazine, the optical density could not be measured in growth experiments in which atrazine was supplied as the sole source of carbon and nitrogen. Therefore, growth was measured by standard plate count technique on trypticase soy agar plates. Selected growth studies were also conducted in stirred bioreactors for convenient aeration and pH measurements.

Analytical Methods

The degradation of atrazine in enrichment cultures and degradation of atrazine and other s-triazines in experiments was evaluated on the basis of the loss of atrazine from media. Samples (0.5 ml) for atrazine analysis were extracted with 0.1 ml of methanol or acetonitrile in microcentrifuge tubes and centrifuged at 15,400 g for 15 minutes. Atrazine was analyzed by reverse phase HPLC using an ABI 400 Solvent Delivery System equipped with an ABI 783A W detector set at 220 nm. Samples containing 50 to 100 μl were injected onto an Alltech C-18 Econosphere column having 5 μm pore size, 25 cm long, with a Spectra Physics SP8875 autosampler and eluted with an isocratic mobile phase consisting of 55% acetonitrile:45% water (vol vol$^{-1}$). HPLC analyses in all other experiments were conducted with either an ABI Spectraflow 400 equipped with an ABI Spectraflow 757 UV detector, or an Altex model 101A HPLC equipped with a Waters Lamda Max model 481 LC spectrophotometer and Waters Data Module integrator.

Simazine and cyanazine were analyzed by gas chromatography using a Varian 3500 gas chromatograph equipped with a Varian 8100 auto sampler. Samples were prepared by removing 0.75 ml aliquots at various times from the culture flasks and extracting the aqueous samples by passage through cyclohexyl solid phase extraction columns. The samples were then eluted with 1.5 ml ethyl acetate and stored at 4° C. until analyzed. Quantification of the samples was based on an internal azobenzene standard. The column used was a 60 m DB-5 column with an 0.25 cm internal diameter and 0.25 μm film thickness. The carrier gas was $H_2$ at 1.5 ml minutes$^{-1}$ with a pressure of 19.7 psi and a velocity of 39.2 cm s$^{-1}$. The operating conditions consisted of split/splitless injection with the injector temperature set at 250° C. The split ratio was 25:1. The initial column temperature was maintained at 120° C. for 0.5 minutes and then increased to 165° C. at 5.5° C. minutes$^{-1}$, to 210° C. at 1.2° C. minutes$^{-1}$ and to a final temperature of 245° C. at a rate of 5.0° C. minutes$^{-1}$. The final temperature was maintained for 7.5 minutes. The total run time was 62.5 minutes. A nitrogen-phosphorus detector was used at an operating temperature of 300° C. and 3.2 A. The detector make-up gas was He at 25–30 ml minutes$^{-1}$. The $H_2$ flow rate was 3–4 ml minutes$^{-1}$ and the air flow was 170–180 ml minutes$^{-1}$.

Evaluation of M91-3

Degradation of s-triazines.

Initially, several triazine herbicides were tested for their ability to support growth of M91-3 in glucose-amended media, where the triazines were the sole source of nitrogen. These triazine compounds were: ametryn (0.1 mM); cyanazine (0.05 mM); a non-symetrical triazine, metribuzin (0.1 mM); prometon (0.1 mM); prometryn (0.1 mM); propazine (0.04 mM); simazine (0.025 mM); and terbutryn (0.1 mM). The concentrations were selected to provide a nitrogen level equivalent to the nitrogen level available where 0.1 mM atrazine is completely degraded. If the concentration of the triazine exceeded the solubility limit, the concentration was reduced. The experiment lasted about 4 weeks. Growth was determined by visual examination; a turbid culture indicated growth.

Growth was not observed when ametryn, metribuzin, prometon, prometryn, propazine, or terbutryn were provided as the sole source of nitrogen. However, M91-3 may have degraded some or all of these compounds, the residual concentrations of the triazines were not quantified at the end of the experiment. The M91-3 grew readily in glucose-amended media with atrazine and simazine, and to a lesser extent with cyanazine as the sole source of nitrogen.

Atrazine Degradation

Accordingly, to examine the M91-3 degredation of atrazine in a variety conditions, atrazine was added to M91-3 cultures in media supplemented with 5.5 mM glucose, ammonium-free media supplemented with 5.5mM glucose and nitrate, ammonium-free media supplemented with 5.5mM glucose, and ammonium-free media. The results are shown in FIGS. 1A through 1D.

Figure 1B:
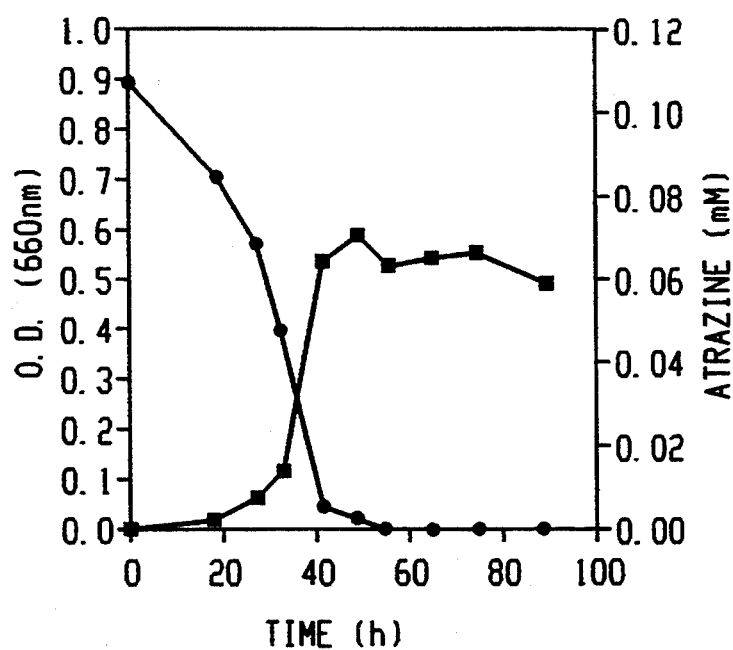
FIG. 1B. is a graph showing M91-3 degradation of atrazine, represented by circles, in ammonium-free media supplemented with glucose and nitrate.
Figure 1C:
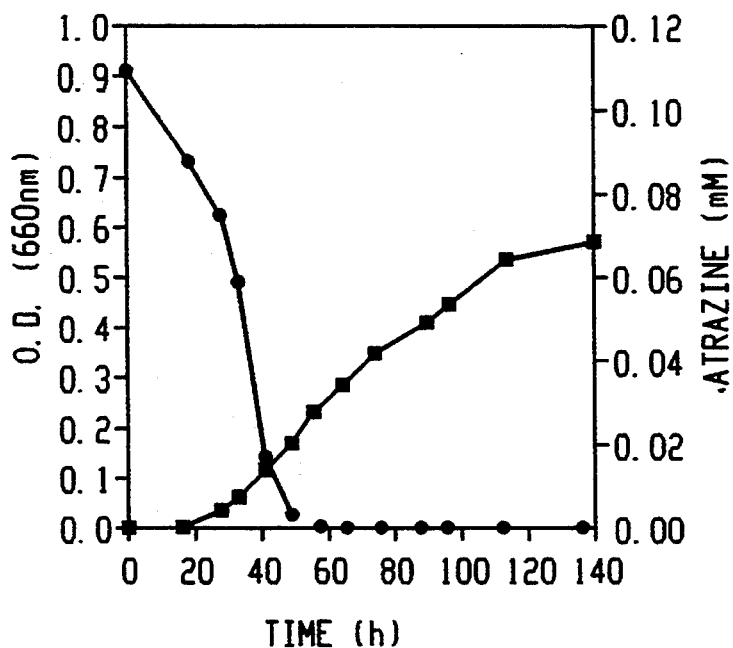
FIG. 1C. is a graph showing M91-3 degradation of atrazine, represented by circles, in ammonium-free media supplemented with glucose.
Figure 1D:
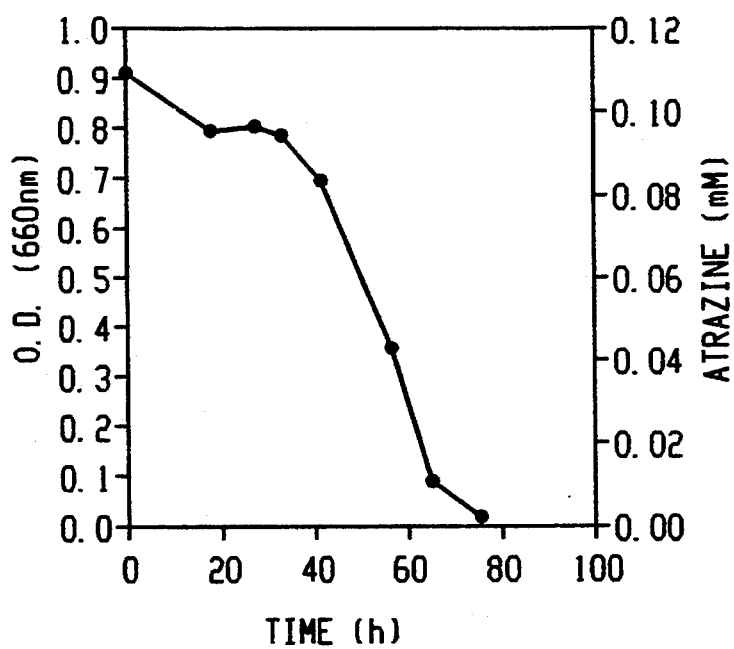
FIG. 1D. is a graph showing M91-3 degradation of atrazine, represented by circles, in ammonium-free media.

M91-3 was able to degrade atrazine under each of the cultural conditions. M91-3 growth in media containing glucose supplement could be measured in terms of optical density and is shown in FIG. 1A–C. In contrast, changes in turbidity were negligible in media supplemented with atrazine as the sole source of carbon and nitrogen. There was no loss of atrazine in the sterile controls. There was no perceptible increase in optical density during atrazine-dependent growth in ammonium-free media with atrazine.

Figure 2:
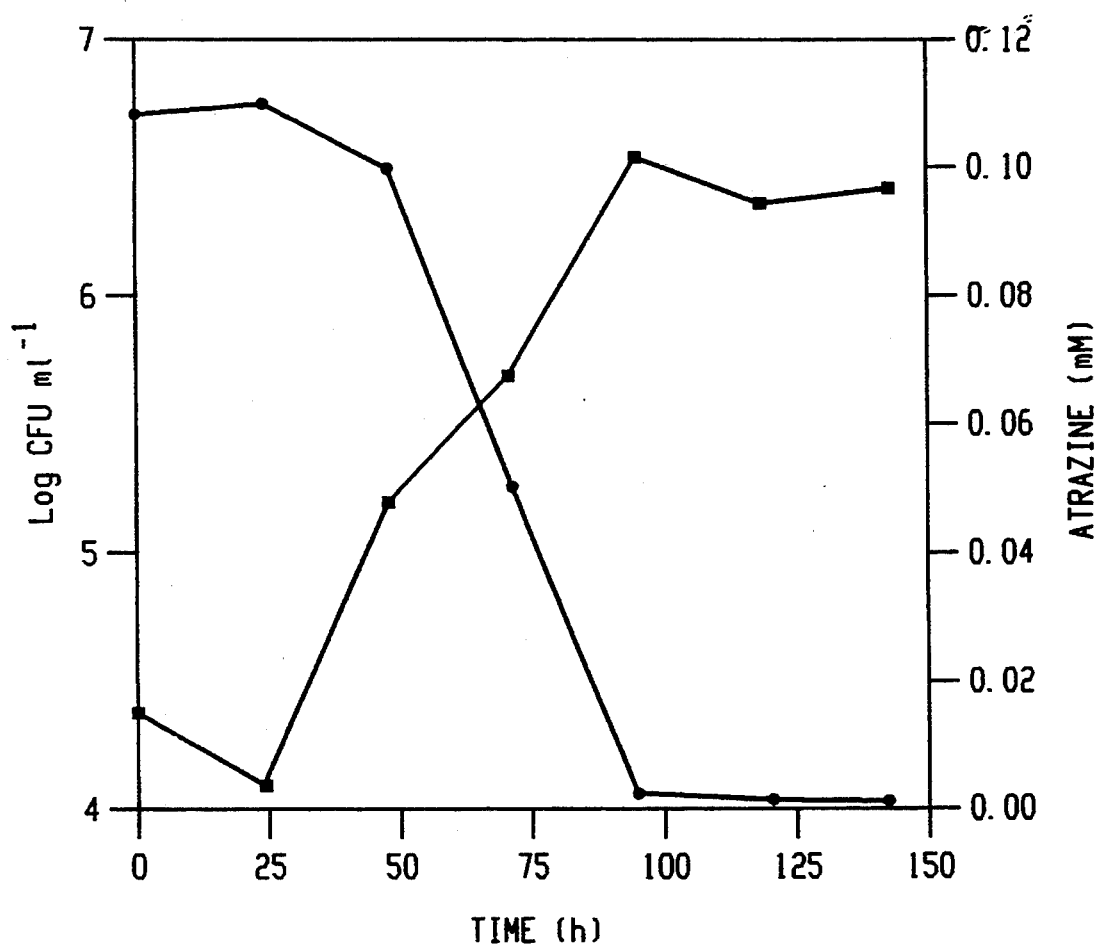
FIG. 2. is a graph showing the growth of M91-3 in ammonium-free media with atrazine measured by colony counts represented by squares. The graph also contains a plot of the residual atrazine concentration represented by circles, over time.

FIG. 2 shows the growth of M91-3 measured as colony counts in media with atrazine as a sole source of carbon and nitrogen. No loss of atrazine was evident in uninoculated, sterile controls. No growth was observed in ammonium-free, atrazine-free media supplemented with glucose, indicating that the observed growth of M91-3 was at the expense of the added atrazine and not the result of N2-fixation. To determine the stability of the atrazine-degrading phenotype M91-3 was subcultured at least five times in atrazine-free media and then reintroduced to media supplemented with glucose. The M91-3 culture rapidly degraded atrazine, indicating that the ability to degrade atrazine was a stable trait.

The degradation of atrazine by M91-3 was also examined in ammonium free media with a 5.5 mM glucose supplement. The M91-3 culture completely degraded atrazine within 50 hours. The growth of the M91-3 culture was slow, linear and continued after atrazine had been depleted. The linear growth was indicative of nutrient-limited growth, possibly due to the slow release of nitrogen from the atrazine molecule. No significant loss of atrazine was observed in the sterile control cultures.

Simazine degradation

Figure 3A:
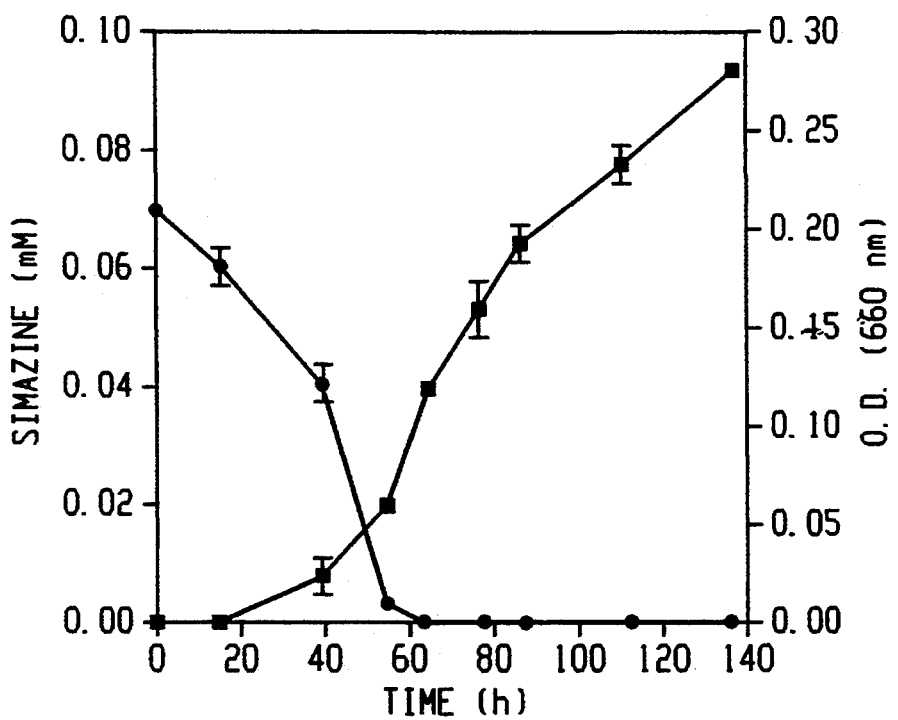
FIG. 3A. is a graph showing M91-3 degradation over time, of simazine, represented by circles, in ammonium-free media supplemented with 1.1 mM glucose. The graph also contains a plot over time of the optical density of the culture, represented by squares.

The degradation of simazine by M91-3 was investigated at a supersaturated concentration of 0.065mM which exceeded its aqueous solubility limit of 0.02 mM. This concentration provided a nitrogen level of 0,325 mM N 1$^{-1}$ which is in the same concentration range as 0.5 mM nitrogen that was present in the atrazine degradation experiments. The results are shown in FIG. 3A.

The simazine degradation proceeded without a lag period and the simazine was completely depleted by about 55 hours. The growth as determined by optical density of M91-3 continued after simazine was completely depleted as show in FIG. 3A. The concentration of simazine in the sterile control remained essentially the same.

Degradation of Cyanazine

Figure 3B:
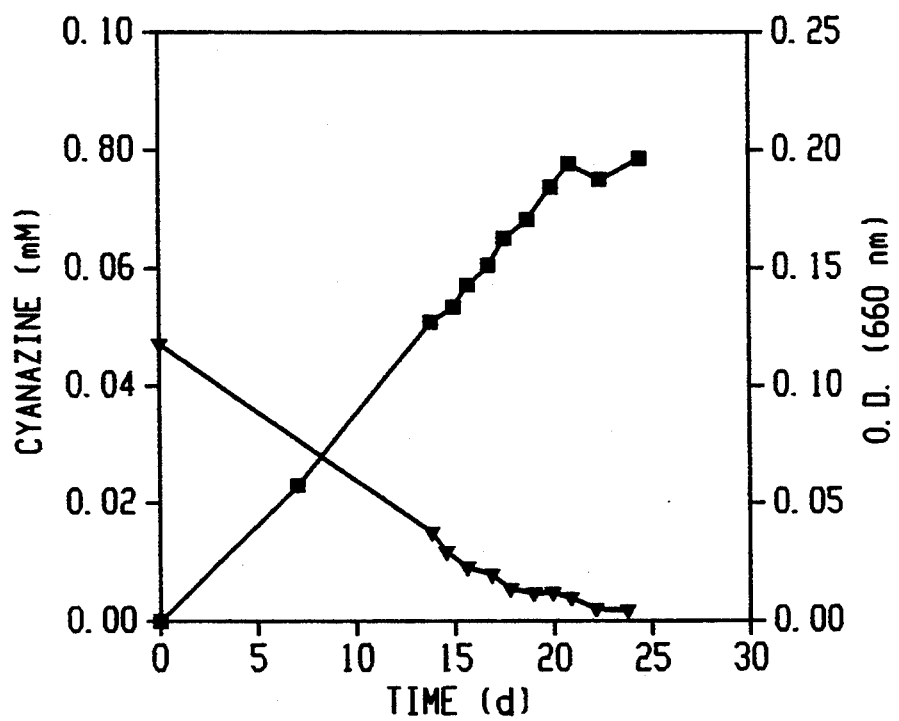
FIG. 3B. is a graph showing M91-3 degradation over time, of cyanazine, represented by inverted triangles, in ammonium-free media supplemented with 1.1mM glucose. The graph also contains a plot over time of the optical density of the culture, represented by squares.

The degradation of cyanizine by M91-3 was investigated at in ammonium-free media supplemented with 1.1mM glucose. The cyanizine concentration was 0.05 mM which is equivalent to 0.30 mM nitrogen. The results are shown in FIG. 3B.

When cyanazine was present as the sole source of nitrogen, the degradation and the cyanizine was slower than when compared to the degradation of either atrazine or simazine. Approximately 25 days elapsed before cyanizine was completely depleted as shown in FIG. 3B. No significant loss of cyanazine Was observed in the sterile control cultures.

Degradation of Binary s-Triazine Mixtures.

The degradation of binary and ternary mixtures of atrazine, simazine, and cyanazine by M91-3 was investigated in nitrogen-free media, with and without glucose as an additional carbon and energy source. Simazine, cyanazine, and atrazine were used at 0.02, 0.05, and 0.1 mM concentrations, respectively. The s-triazine mixtures were inoculated with early stationary phase cultures of M91-3 grown in media which contained glucose as a carbon and energy source and one of the s-triazines as the sole nitrogen source.

A mixture of 0.1 mM atrazine and 0.02 mM simazine were added to M91-3 cultures supplemented with 2.2mM glucose. The atrazine and simazine concentration in the media was examined at various time points as indicated in FIG. 4A.

Figure 4A:
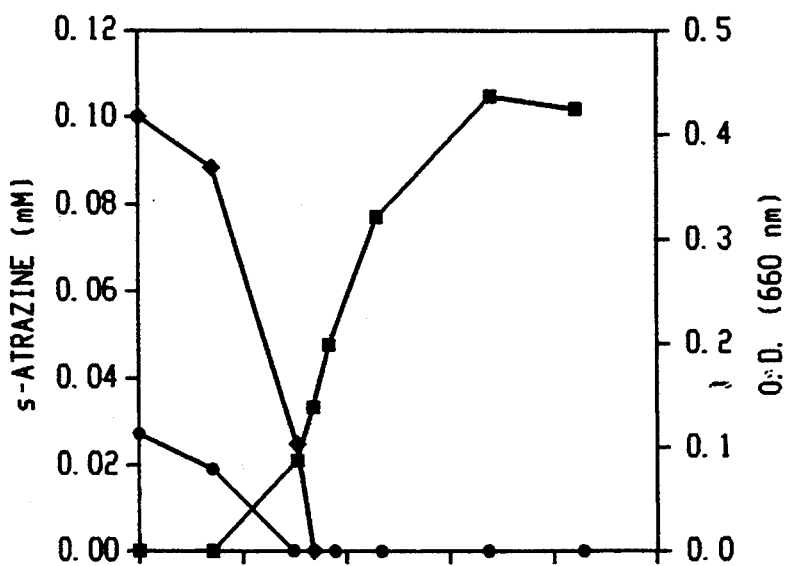
FIG. 4A. is a graph showing M91-3 degradation of a binary mixture of s-triazines composed of 0.1 mM atrazine and 0.03 mM simazine, in ammonium-free media supplemented with 2.2 mM glucose. The atrazine level in the media is represented by diamonds and the simazine level in the media is represented by circles. The graph also contains a plot over time of the cell density, as measured by optical density, which is represented by squares.

Both the atrazine and simazine were completely depleted by M91-3, without a lag period within 50 hours as shown in FIG. 4A. Growth of the M91-3 culture reached a maximum optical density of 0.43 which was in keeping with the doubling of the glucose concentration and of the available nitrogen provided by the combination of the atrazine and simazine as shown in FIG. 4A.

Figure 4B:
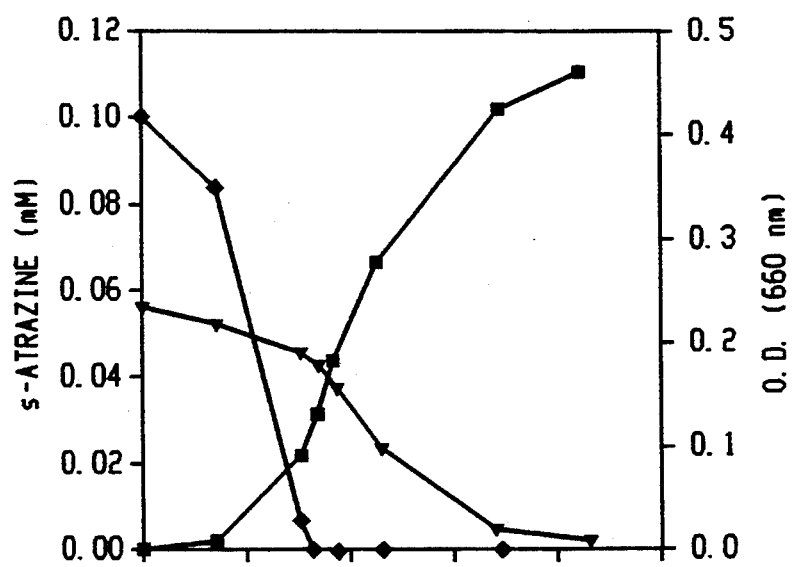
FIG. 4B. is a graph showing M91-3 degradation of a binary mixture of s-triazines composed of 0.1 mM atrazine and 0.054 mM cyanazine, in ammonium-free media supplemented with 2.2 mM glucose. The atrazine level in the media is represented by diamonds and the cyanazine level in the media is represented by inverted triangles. The graph also contains a plot over time of the cell density, as measured by optical density, which is represented by squares.

A culture of M91-3 was supplemented with 2.2 mM glucose and a mixture of 0.1mM atrazine, and 0.05mM cyanazine. The atrazine and cynazine concentration in the media was examined at various time points as indicated in FIG. 4B.

The cyanazine completely disappeared from the M91-3 cultures within 125 hours. The maximum optical density was equivalent to that obtained in the culture that received the atrazine/simazine mixture. The results suggested that atrazine was required for complete induction of the s-triazine degradative system.

Accordingly, an experiment was conducted where cyanazine was provided as the sole nitrogen source in an atrazine-induced M91-3 culture used as an inoculum. The M91-3 inoculum was grown, harvested at mid-exponential phase and the cells were washed three times with phosphate buffered saline. The cells were then added to glucose supplemented media containing 0.05 mM cyanazine.

The pre-induced M91-3 cells did not significantly enhance cyanazine degradation during a 125 hour incubation. The results of this experiment failed to explain the enhanced degradation of cyanazine in the presence of atrazine.

Cultures of M91-3 received a binary mixture of simazine and cyanazine in media supplemented with 2.2 mM glucose. The simazine and cyanazine concentration in the media was examined at various time points as indicated in FIG. 4C.

Figure 4C:
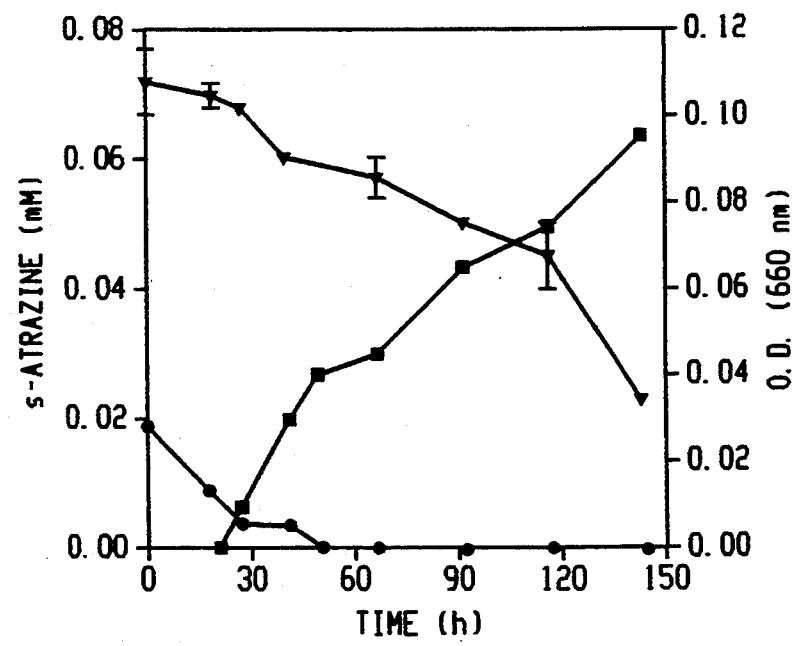
FIG. 4C. is a graph showing M91-3 degradation of a binary mixture of s-triazines composed of 0.02 mM simazine and 0.07 mM cyanazine, in ammonium-free media supplemented with 2.2 mM glucose. The simazine level in the media is represented by circles and the cyanazine level in the media is represented by inverted triangles. The graph also contains a lot over time of the cell density, as measured by optical density, which is represented by squares.

The culture growth was not influenced by cyanazine as shown in FIG. 4C. The degradation of cyanazine, however, was enhanced but to a lesser extent than observed in the culture that received the mixture of atrazine and cyanazine. The cell density of the culture reached an optical density of 0.10 after 144 hours of incubation.

Degradation of Ternary s-Triazine Mixtures.

The cultures of M91-3 received a ternary mixture of s-triazines, containing simazine, cyanazine, and atrazine in media supplemented with 3.3mM glucose. The three s-triazines served as the sole source of nitrogen. The results are shown in in FIG. 5A.

Figure 5A:
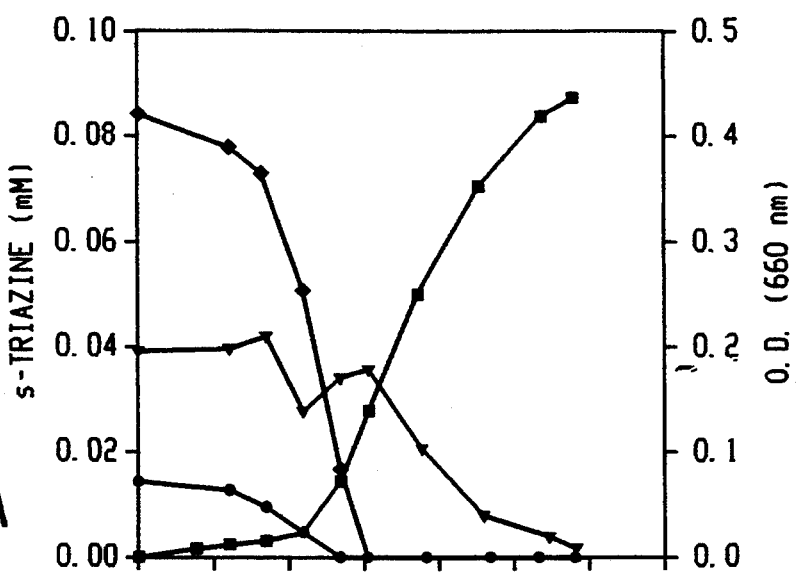
FIG. 5A. is a graph showing M91-3 degradation over time of ternary mixture of s-triazines composed of: atrazine, represented by diamonds; simazine, represented by circles; and cyanazine, represented by triangles; in ammonium-free media supplemented with 3.3 mM glucose. The M91-3 inoculum was from a culture previously grown with atrazine as the sole nitrogen source. The graph also contains a plot of the optical density of the culture over time, represented by squares.

As in the binary mixture experiments, atrazine and simazine were completely degraded within 50 hours, as shown in FIG. 5A. The cyanazine was completely degraded in 144 hours. The degradation of cyanazine was delayed until the atrazine and simazine were almost completely depleted. The results suggested that there was no apparent difference in the specificity of the s-triazine-degrading enzymes of the M91-3 for atrazine and simazine. The slow rate of cyanazine degradation may reflect reduced specificity of the s-triazine-degrading enzymes for cyanazine. Alternatively, cyanazine degradation may require an additional initial rate-limiting enzymatic step.

Additional experiments on ternary mixtures were conducted to examine the effect of previous growth substrate on s-triazine degradation. An M91-3 inoculum, taken from a culture grown on atrazine as the sole nitrogen source, was added to media supplemented with 3.3 mM glucose and the ternary mixture of simazine, cyanazine, and atrazine. A second M91-3 inoculum, taken from a culture grown on simazine as the sole nitrogen source, was added to media supplemented with 3.3 mM glucose and the ternary mixture of s-triazines. A third M91-3 inoculum, taken from cultures grown on cyanizine as the sole nitrogen source, was added to media supplemented with 3.3 mM glucose and the ternary mixture of s-triazines.

Figure 5B:
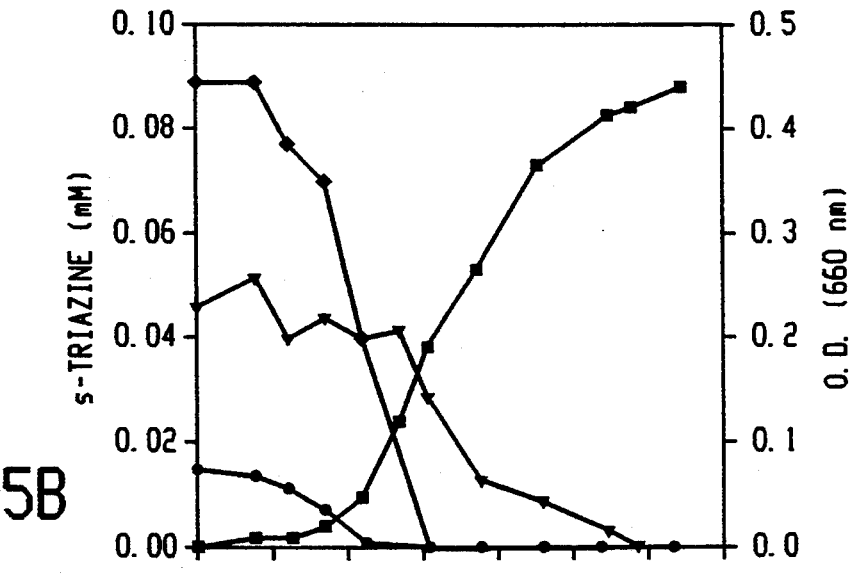
FIG. 5B. is a graph showing M91-3 degradation over time of ternary mixture of s-triazines composed of: atrazine, represented by diamonds; simazine, represented by circles; and cyanazine, represented by triangles; in ammonium-free media supplemented with 3.3 mM glucose. The M91-3 inoculum was from a culture previously grown with simazine as the sole nitrogen source. The graph also contains a plot of the optical density of the culture over time, represented by squares.
Figure 5C:
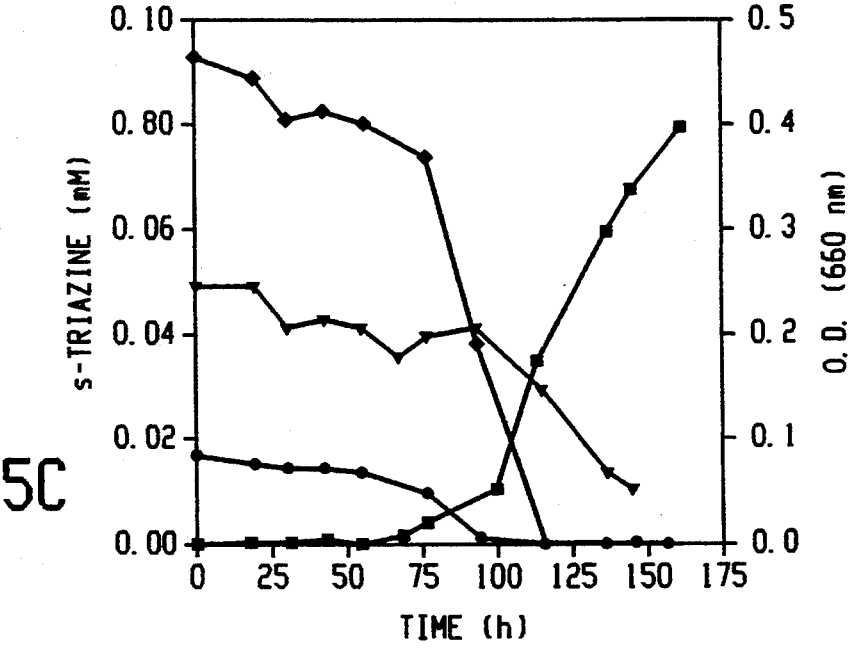
FIG. 5C. is a graph showing M91-3 degradation over time of ternary mixture of s-triazines composed of: atrazine, represented by diamonds; simazine, represented by circles; and cyanazine, represented by triangles; in ammonium-free media supplemented with 3.3 mM glucose. The M91-3 inoculum was from a culture previously grown with cyanazine as the sole nitrogen source. The graph also contains a plot of the optical density of the culture over time, represented by squares.

There was no difference in the degradation of the atrazine, cyanazine or simazine when the M91-3 inoculum was grown with either atrazine or simazine as the nitrogen source as shown in FIG. 5A and 5B. However, when the M91-3 had been previously grown in media containing glucose, with cyanazine as the sole source of nitrogen, the degradation of atrazine, simazine and cyanazine was delayed. Also, as shown in FIG. 11C, the growth of the culture was delayed. However, the subsequent active phase of herbicide utilization and the final cell density of the culture were comparable to those in other experiments.

Experiments were also performed in which cultures of M91-3 in media lacking a glucose supplement received the ternary mixture of the s-triazines. The results are shown in FIG. 6.

Figure 6:
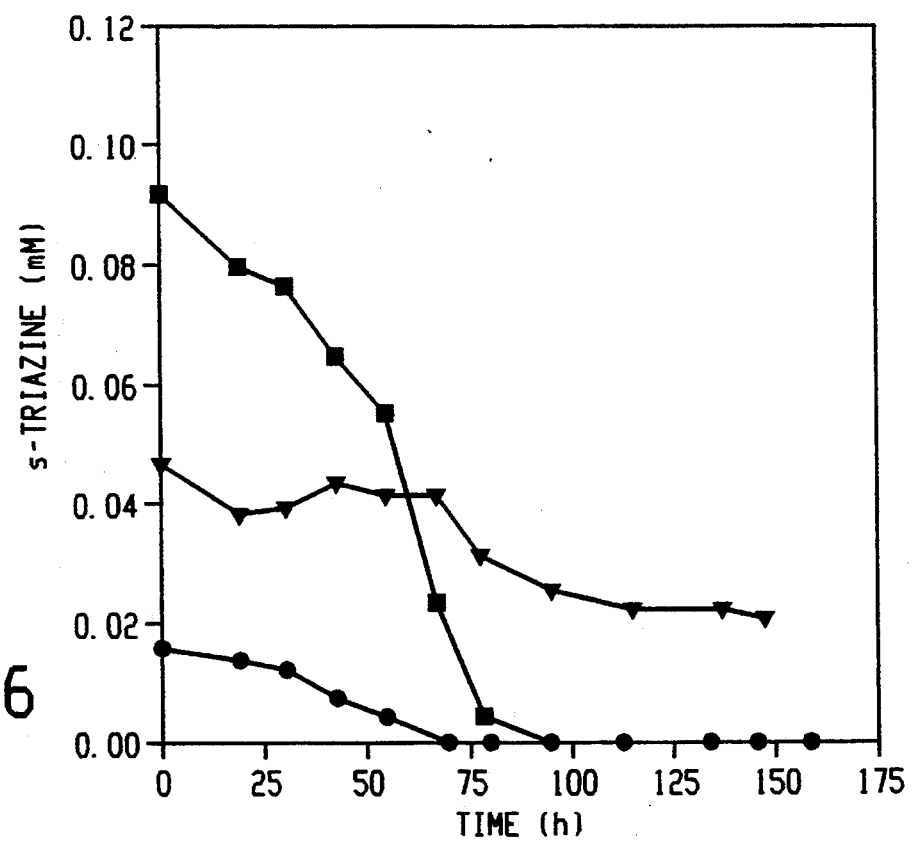
FIG. 6. is a graph showing M91-3 degradation over time of a ternary mixture of s-triazines composed of atrazine, represented by diamonds, simazine, represented by circles, and cyanazine represented by triangles in ammonium-free media. The s-triazines served as the sole source of carbon and nitrogen.

The atrazine, simazine and cyanazine were completely or partially depleted from the cultures containing a ternary mixture which did not receive a glucose amendment as shown in FIG. 6.

Thus, in addition to atrazine, the M91-3 is capable of deriving nitrogen by the degradation of two other s-triazines, cyanazine and simazine. Since the M91-3 did not grow in media lacking an exogenous nitrogen source such as $NH_4^+$ or an s-triazine, M91-3 does not actively fix $N_2$. Apparently, only the side chains in s-triazines serve as a carbon source for the M91-3, because the carbon in the ring structure has a +IV valence and the M91-3 would require a reductive system for assimilation. However, only a limited amount of carbon was available from the degradation owing to the poor solubility of the s-triazines in aqueous solutions. Thus the carbon and energy source needed for growth is limited. A primary carbon source, glucose, was used to reach high cell densities in culture media, but glucose was not essential for the s-triazine degradation, nor did glucose suppress the degradative activity of the M91-3. The M91-3 was able to utilize simazine and cyanazine as nitrogen sources for glucose-dependent growth. The M91-3 used atrazine and simazine indiscriminately, whereas cyanazine degradation was slow and delayed until the depletion of the simazine and atrazine.

Figure 7:
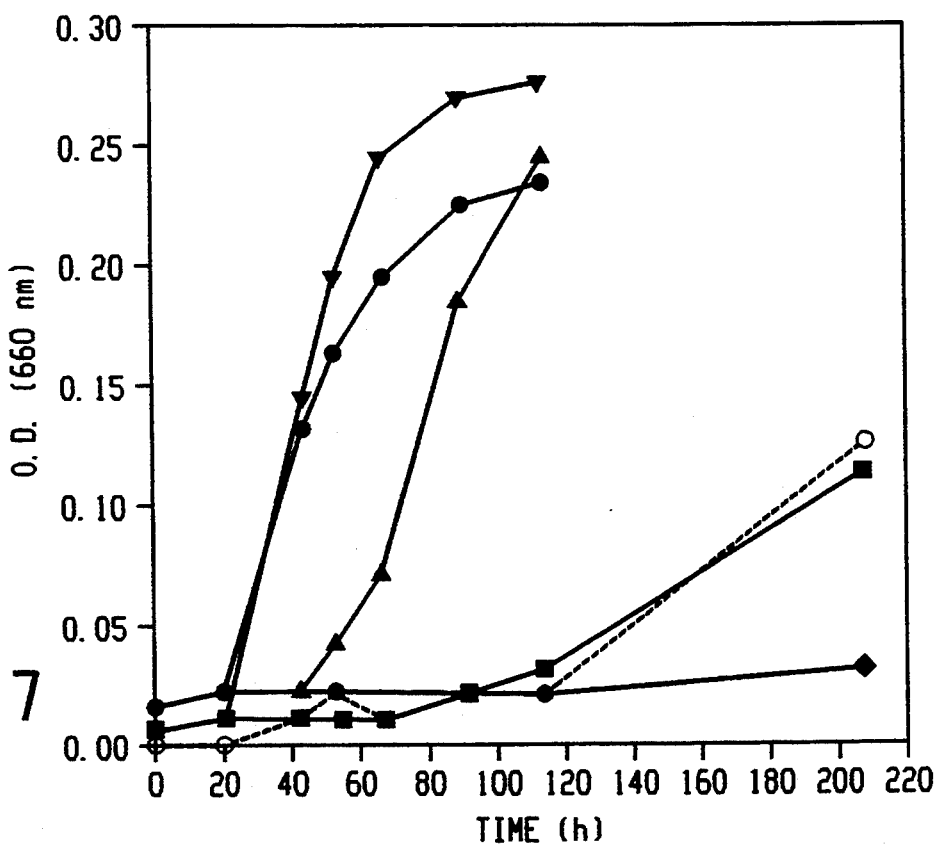
FIG. 7. is a graph showing the growth of M91-3 cultures, as measured by optical density when utilizing various s-triazine intermediates as nitrogen sources in ammonium-free media containing glucose as the carbon and energy source. 2-Chloro-4-amino-6-isopropylamino-s-triazine is represented by solid circles; 2-Chloro-4-ethylamino-6-amino-s-triazine is represented by inverted triangles; CAAT is represented by squares; 2-Hydroxy-4,6-diamino-s-triazine is represented by upright triangles; 2-Hydroxy-4-amino-6-isopropylamino-s-triazine is represented by diamonds; 2-Hydroxy-4-ethylamino-6-isopropylamino-s-triazine is represented by open circles and dashed lines.
Figure 8:
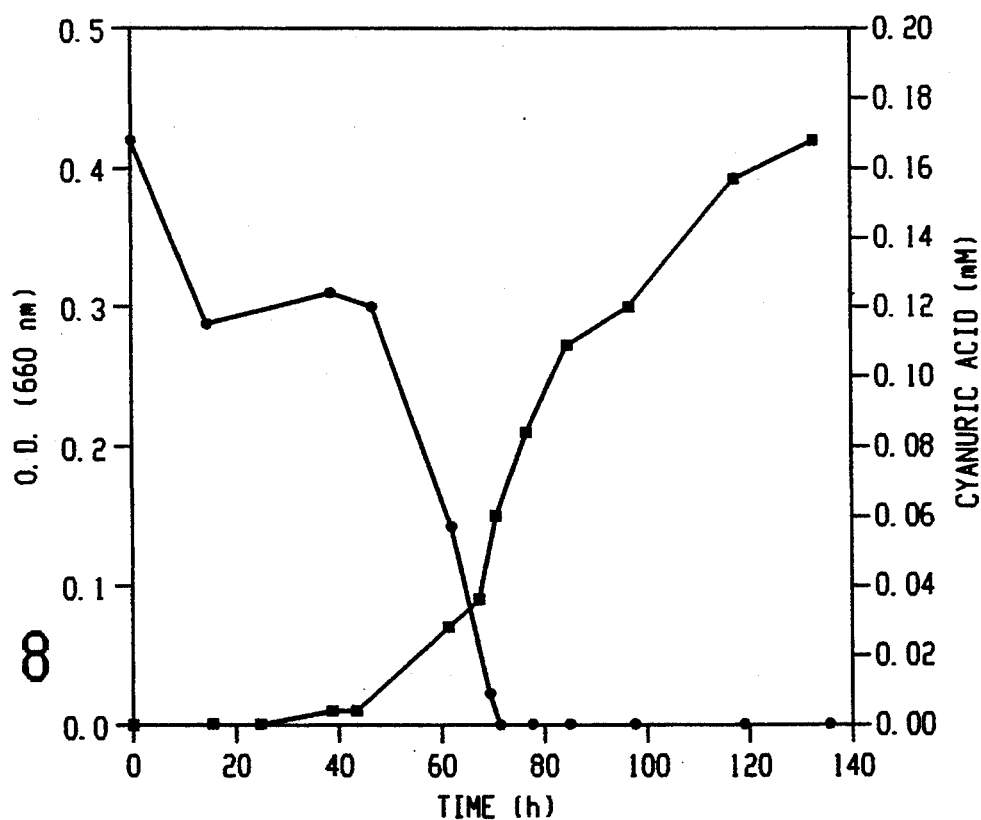
FIG. 8. is a graph showing the growth of M91-3 cultures as measured by optical density represented by squares, when utilizing 2,4,6-Trihydroxy-s-triazine as a nitrogen source in ammonium-free media containing glucose as the carbon and energy source. The graph also contains a plot of the residual cyanuric acid concentration over time represented by circles.
Figure 9:
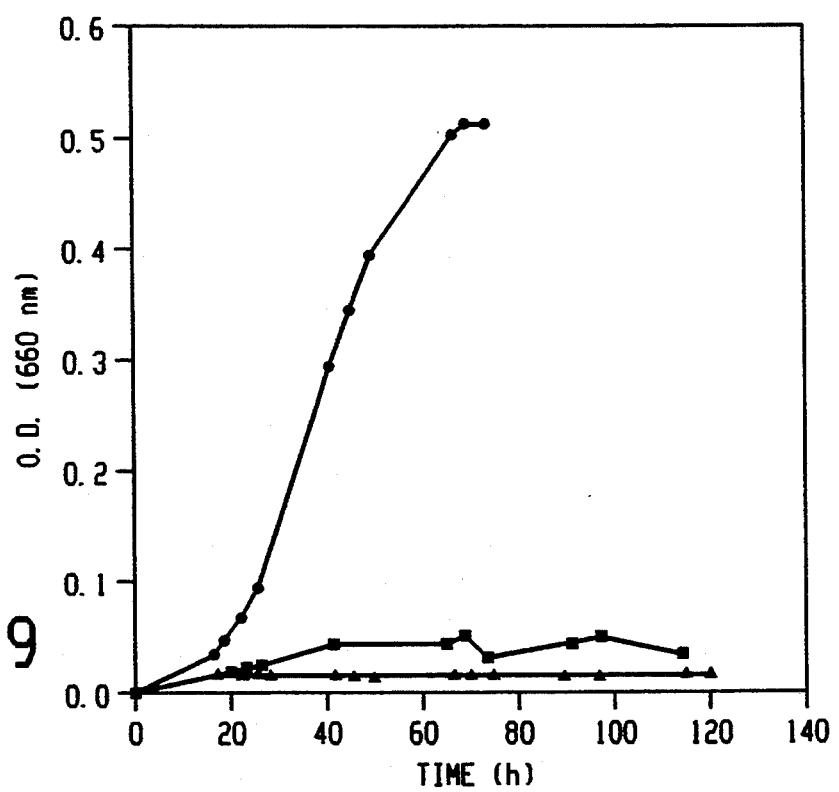
FIG. 9. is a graph showing the growth of M91-3 cultures as measured by optical density when utilizing biuret represented by circles, urea represented by squares, and melamine represented by triangles as nitrogen sources by M91-3 in ammonium-free media containing glucose as the carbon and energy source.

To determine whether M91-3 could utilize other s-triazines and proposed potential metabolites of s-triazine as sole sources of nitrogen, the following compounds: 2-Chloro-4-amino-6-isopropylamino-s-triazine, 2-Chloro-4-ethylamino-6-amino-s-triazine, 2-Chloro-4,6-diamino-s-triazine, 2-Hydroxy-4,6-diamino-s-triazine, 2-Hydroxy-4-ethylamino-6-isopropylamino-s-triazine, 2-Hydroxy-4-amino-6-isopropylamino-s-triazine; melamine; cyanuric acid; biuret; melamine; and urea were added to cultures of M91-3 in ammonium free glucose-supplemented media. Metribuzin, which is not an s-triazine, was added for comparison. The concentrations of these compounds were standardized relative to the nitrogen content of 0.1 mM atrazine. All compounds were added at 0.10 mM, except melamine was added at 0.08 mM and cyanuric acid which was added at 0.17 mM. The growth of the cultures were monitored by changes in turbidity as measured by optical density. The results are shown in FIGS. 7, 8, and 9.

The M91-3 was capable of utilizing 2-Chloro-4-amino-6-isopropylamino-s-triazine, 2-Chloro-4-ethylamino-6-amino-s-triazine, 2-Chloro-4,6-diamino-s-triazine, 2-Hydroxy-4,6-diamino-s-triazine, and 2-Hydroxy-4-ethylamino-6-isopropylamino-s-triazine as nitrogen sources when provided with glucose as a carbon source. 2-Hydroxy-4-amino-6-isopropylamino-s-triazine and melamine did not support growth. As shown in FIG. 8, cyanuric acid served as a nitrogen source, indicating that the M91-3 cleaved the s-triazine ring. As shown in FIG. 9, negligible growth was observed when biuret or melamine was supplied as an N-source, whereas urea supported growth.

Degradation by Non-Growing Cells

To investigate the inducibility of the s-triazine degradation by M91-3, a M91-3 culture was grown to early stationary phase in ammonium-free media with atrazine and 5.5 mM glucose. A second M91-3 culture was grown in medium supplemented $NH_4^+$, but lacking atrazine After the cultures reached early stationary phase, about three days, the cells from both cultures were harvested by centrifugation and washed three times in phosphate buffer having a pH of 7.2. The cultures were separately resuspended in a tris-HCl buffer solution containing atrazine. Samples of the cell suspensions were taken at 2 hour intervals over a period of 8 hours and analyzed by HPLC to determine the loss of atrazine due to degradation.

Figure 10:
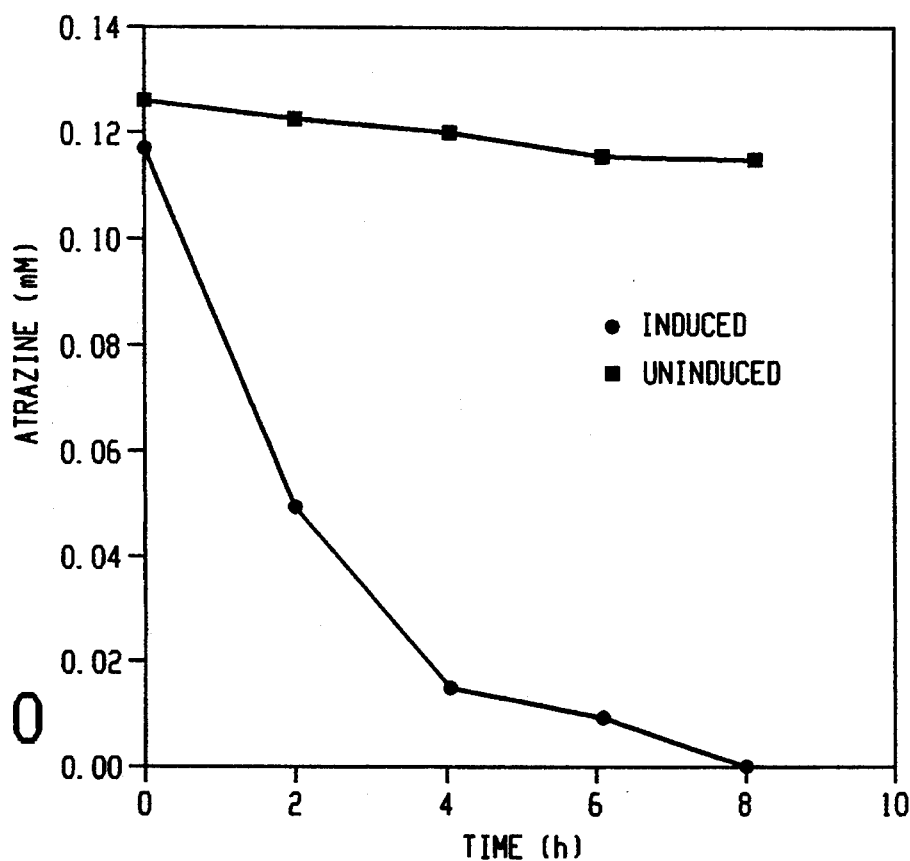
FIG. 10. is a graph showing atrazine degradation over time in tris-HCl buffer by induced resting M91-3 cell suspensions, represented by circles and uninduced resting M91-3 cultures; represented by squares.

As shown in FIG. 10, the atrazine completely disappeared within eight hours from the culture containing the M91-3 that was previously grown with atrazine. The disappearance of atrazine in this suspension appeared to follow first-order kinetics with a rate constant of $-0.44$ $h^{-1}$. In contrast, only a minimal amount of atrazine disappeared from the culture containing the M91-3 cells previously grown in the absence of atrazine as shown in FIG. 10. Thus, the atrazine degradative activity of M91-3 was inducible. Under aerobic conditions, exogenous $NH_4^+$ and $NO_3^-$ did not directly stimulate or suppress the degradation of atrazine. However, data from the stirred bioreactor experiments showed that exogenous inorganic nitrogen directly influenced the catabolism of glucose, being either net acid-producing with ammonium or net acid-consuming with nitrate supplementation. The biochemical mechanism of the influence of ammonium and nitrate on glucose respiration is not known.

M91-3 Anaerobic Degradation of Atrazine

The ability of M91-3 to degrade atrazine under anaerobic conditions was determined. The medium was prepared under an atmosphere of $CO_2:H_2$ (90:10 $vol^{-1}$). Serum bottles containing 40 ml of media were inoculated with a 1% inoculum volume $vol^{-1}$ M91-3. Cultures were prepared containing ammonium-free-media supplemented with either atrazine or atrazine and glucose. Cultures were also prepared containing atrazine, glucose and $NH_4^+$ and atrazine, glucose and $NO_3^-$. Uninoculated control cultures containing glucose, $NH_4^+$ and atrazine were also prepared. The cultures were incubated at 25° C. in the dark. Samples (0.5 ml) were removed periodically with a sterile syringe for HPLC analysis, and optical density analysis.

Figure 11:
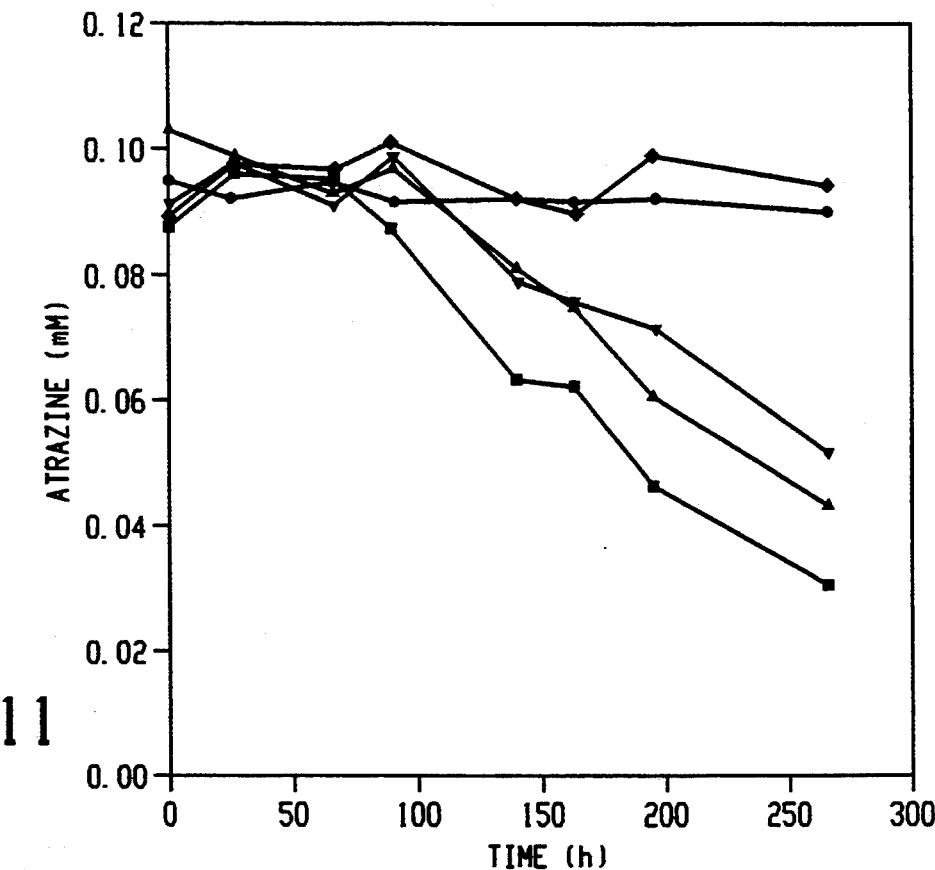
FIG. 11. is a graph showing anaerobic degradation over time of atrazine by M91-3 in different media with various supplements: glucose and $NH_4^+$ represented by circles; glucose and $NO_3^-$ represented by squares; glucose, represented by upright triangles; atrazine as sole carbon and nitrogen source, represented by inverted triangles; and uninoculated media with atrazine supplemented with glucose and $NH_4^+$ as an abiotic control, represented by diamonds.

The M91-3 degraded atrazine in the absence of $O_2$ as shown in FIG. 11. There was no loss of atrazine in uninoculated controls.

Atrazine was also degraded in an additional experiment in which atrazine was provided as the sole source of carbon in the presence of $NO_3^-$ (data not shown). Thus, under anaerobic conditions, atrazine was degraded at reduced rates and the degradation was completely inhibited when the medium was supplemented with $NH_4^+$. The data suggested that the M91-3 was able to couple atrazine degradation to denitrification. The pathway of atrazine transformation under anaerobic conditions is unknown.

Ammonium and Chloride Release

To determine the pathway of atrazine degradation by M91-3, the ammonium and chloride ion release was examined from M91-3 culture utilizing atrazine as the sole carbon and nitrogen source. One liter cultures of M91-3 were prepared in ammonium-free media with either 5.5 mM glucose or without glucose and with 0.1 mM atrazine. The cultures were grown in 3-1 Sternbach flasks and sampled at 2 hour intervals to isolate and identify stable or transient metabolic intermediates during the degradation of atrazine. Samples were taken and split and processed for reverse-phase HPLC, normal-phase HPLC, and for $NH_4^+$ and $Cl^-$ analyses. The dealkylated atrazine derivatives and 2-hydroxyatrazine were analyzed by reverse-phase HPLC using a C-18 solid phase and a mobile phase consisting of 20:80 (vol $vol^{-1}$) acetonitrile and water. The release of ammonium during atrazine mineralization was measured using the indole-phenol blue method.

Chloride-release experiments were conducted in chloride-free basal salts media, in which the chloride salts were replaced with the corresponding sulfate salts at equimolar concentrations. The media were supplemented with and without glucose as above. The media also contained 0.1 mM atrazine. The chloride ion release and atrazine concentration were determined at 2 hour intervals as discussed above. The chloride ion release was measured coulombmetrically using a Haache-Buchler chloridometer. The results are shown in FIG. 12.

Figure 12:
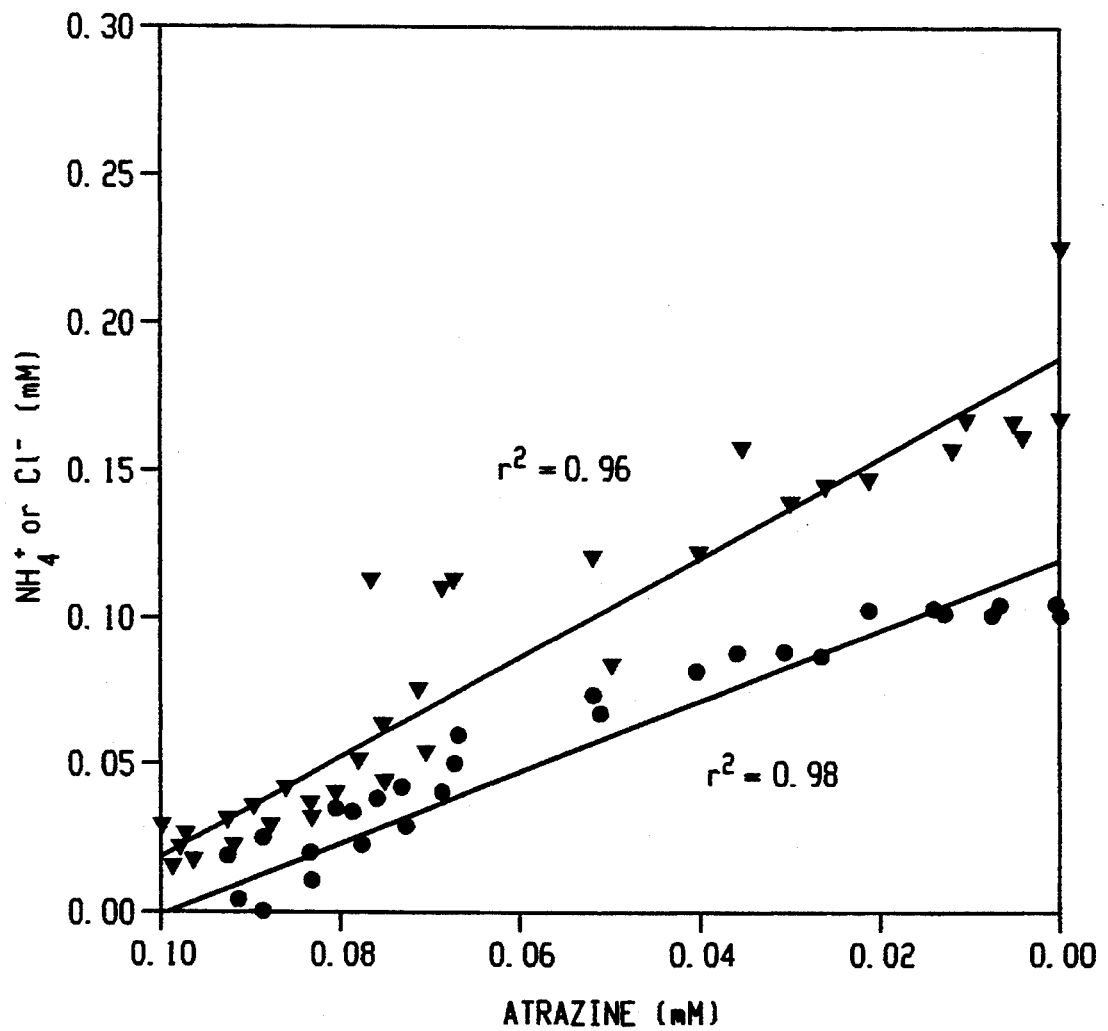
FIG. 12 is a graph showing the release of ammonium and chloride during the degradation of atrazine by the M91-3 culture in ammonium-free mineral salts medium supplemented with 0.1 mM atrazine as the sole source of carbon and nitrogen. Triangles represent the ammonium and circles represent the chloride.

As shown in FIG. 12, in the ammonium-free, glucose-free media, approximately two moles of $N_4^+$ were released per moles NH $^+$of atrazine degraded, leaving three moles of nitrogen unaccounted for. The missing nitrogen either remained in solution as an unidentified metabolite, was volatilized as ammonia, or was assimilated. Chloride ions were released stoichiometrically with respect to atrazine degradation. Accumulation of $NH_4^+$ was not observed in cultures growing in ammonium-free media with glucose, suggesting that the culture was nitrogen limited. Thus, the M91-3 was capable of utilizing atrazine as the sole source of both carbon and nitrogen. M91-3 was also capable of utilizing atrazine as the sole source of nitrogen in mineral salts media supplemented with glucose. The M91-3 has demonstrated the ability to dehalogenate, dealkylate, and deaminate the atrazine.

Mineralization of Atrazine in Solution

Mineralization of (U-$^{14}$C-ring)-atrazine was measured in nitrogen-free media with atrazine supplied as the sole source of carbon and nitrogen, and also in ammonium-free media with atrazine and glucose as the carbon source. The experiments were conducted using 0.1 mM (U-ring-$^{14}$C)-atrazine, having a specific activity 0 2 $\mu$Ci $\mu mol^{-1}$, in 50 mL of media in 125 mL conical flasks sealed with two-holed rubber stoppers for inlet aeration and exhaust ports. The flasks were sparged with filter-sterilized air and exhaust gases were passed through 10 mL 1 N KOH to trap $^{14}CO_2$. One milliliter samples were taken from the traps at four hour intervals and replaced with an equivalent volume of fresh KOH solution. Two aliquots of the culture liquid were taken periodically. One aliquot was used to measure loss of atrazine by HPLC analysis and the other was filtered through nylon membrane to remove cells. The filters were washed, placed in scintillation vials containing 10 ml of scintillation cocktail Scintiverse BD, from Fisher Scientific and the radioactivity was counted on a Beckman LS8000 liquid scintillation counter.

Figure 13A:
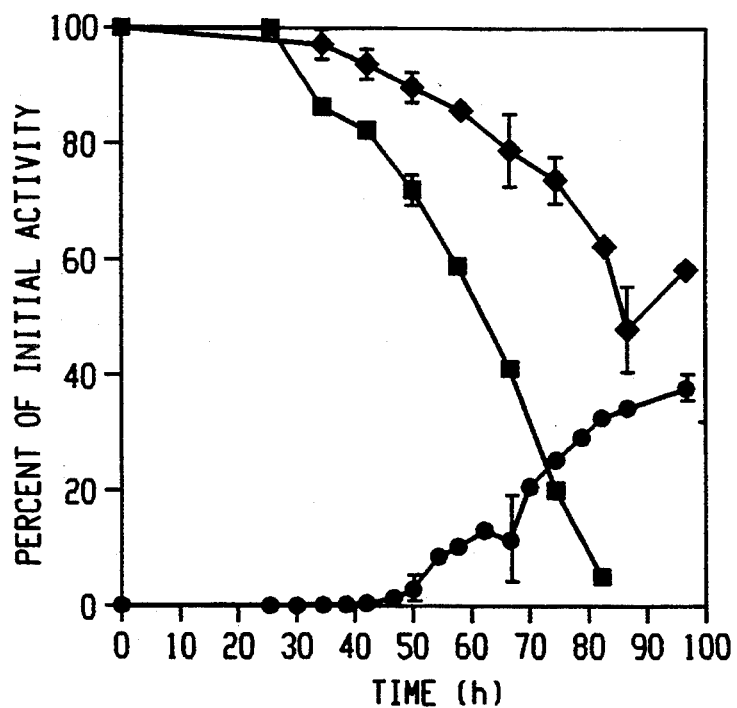
FIG. 13A. is a graph showing the mineralization of U-$^{14}$C-ring-atrazine by M91-3 in ammonium free medium with 0.1 mM atrazine as the sole source of carbon and nitrogen. Circles represent evolved $^{14}CO_2$, diamonds represent the radioactivity in solution and squares represent the residual atrazine measured by HPLC.
Figure 13B:
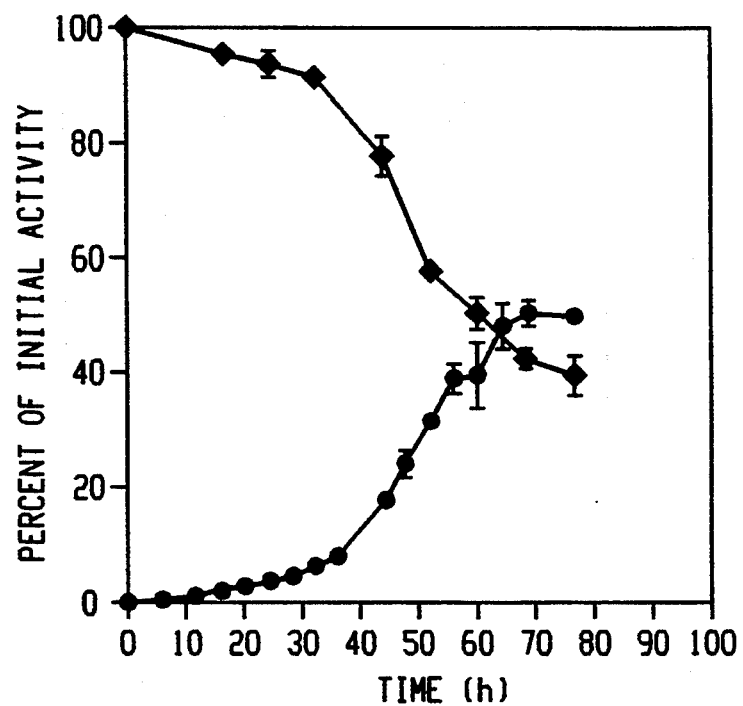
FIG. 13B. is a graph showing the mineralization of U-$^{14}$C-ring-atrazine by M91-3 in ammonium free medium with 0.1 mM atrazine as the sole source of nitrogen and with glucose as the carbon source. Circles represent evolved $^{14}CO_2$, diamonds represent the radioactivity in solution and squares represent the residual atrazine measured by HPLC.

As shown in FIG. 13A, when atrazine served as the sole source of carbon and nitrogen, atrazine was completely degraded within 90 hours of incubation. Approximately 40% of the initial radioactivity was recovered as $^{14}CO_2$, with slightly less than 60% of the activity remaining in solution. Negligible radioactivity was retained on the filters, indicating that the solution activity was not associated with cell biomass. The assimilation of the ring-carbon of atrazine was not expected due to its fully oxidized valence. As shown in FIG. 13B, when glucose was provided as a carbon source, 50% of the added label was recovered as $^{14}CO_2$ with approximately 40% of the activity remained in solution. Less than 3% of the added radioactivity was associated with cells retained on the filters in both experiments.

The loss of atrazine was concurrently determined by HPLC. The HPLC data indicated that little or none of the remaining radioactivity from solution was in the form of atrazine. The atrazine had completely disappeared within 85 hours, suggesting the accumulation of a metabolic end product. Metabolites were not detected by either reverse- or normal-phase HPLC in samples of culture solutions.

A mineralization experiment was conducted in which 0.1 mM (U-$^{14}$C-ring)-atrazine, having a specific activity 0.4 $\mu$Ci $\mu$mol$^{-1}$, was added to ammonium-free medium supplemented with 1.1 nM glucose. The M91-3 inoculum was added and 1 ml samples of the culture medium were taken after the $^{14}CO_2$ evolution had ceased. The samples were centrifuged to remove the cells and thin layer chromatography was performed using standard biuret and urea solutions to check for the presence of biuret and urea. The mobile phase consisted of 40% t-butyl alcohol, 30% methyl ethyl ketone, 10% ammonium hydroxide, and 20% water (vol vol$^{-1}$). After the plates were developed with the mobile phase, they were air dried, and the outer third of the plate (the lane containing the $^{14}$C-labelled sample of culture medium) was divided into 1-cm sections, scraped from the plate and transferred to scintillation vials for counting of the radioactivity. The biuret and urea standards were visualized by reaction with a 4-dimethylaminobenzaldehyde color reagent. The relative mobilities of the biuret and urea were determined and compared to the relative mobility of the radioactivity on the plate.

The thin layer chromatography data showed the presence of urea and biuret in spent culture media, based on co-migration with standards. The majority of the radioactivity present in the spent culture medium migrated with the solvent front, which indicates the presence of an additional hydrophobic metabolite. After an additional 48 hours, the relative concentration of this unidentified hydrophobic metabolite, decreased in the culture medium. The identification of biuret in the media established that the side chains we removed from the atrazine ring, and indicated that the ring was cleaved.

Effect of Soil on M91-3 Degradation of Atrazine

The extent of the evolution of $^{14}CO_2$ from sterile and non-sterile sediments and subsurface sediments inoculated with the M91-3 was determined. Biometers were constructed from 50 mL serum bottles, with 1.5 mL autosampler vials suspended from butyl rubber stoppers. The vials were filled with 1 mL of 1 N KOH trapping solution. Five grams of each sediment were added to sterilized serum bottles and either (U-$^{14}$C-ring) atrazine or (2-$^{14}$C-ethyl)-atrazine was added to provide an initial atrazine concentration of 2.4 mg Kg$^{-1}$. All biometers were inoculated to an initial cell density of $4.5 \times 10^7$ cells g$^{-1}$ and incubated at either 10° or 25° C. All treatments were prepared in duplicate and sterilized uninoculated sediments were included as abiotic controls. The biometers were periodically sampled by changing the traps. The collected trapping solution volume was placed in scintillation vials containing scintillation cocktail and the radioactivity was measured.

Figure 14A:
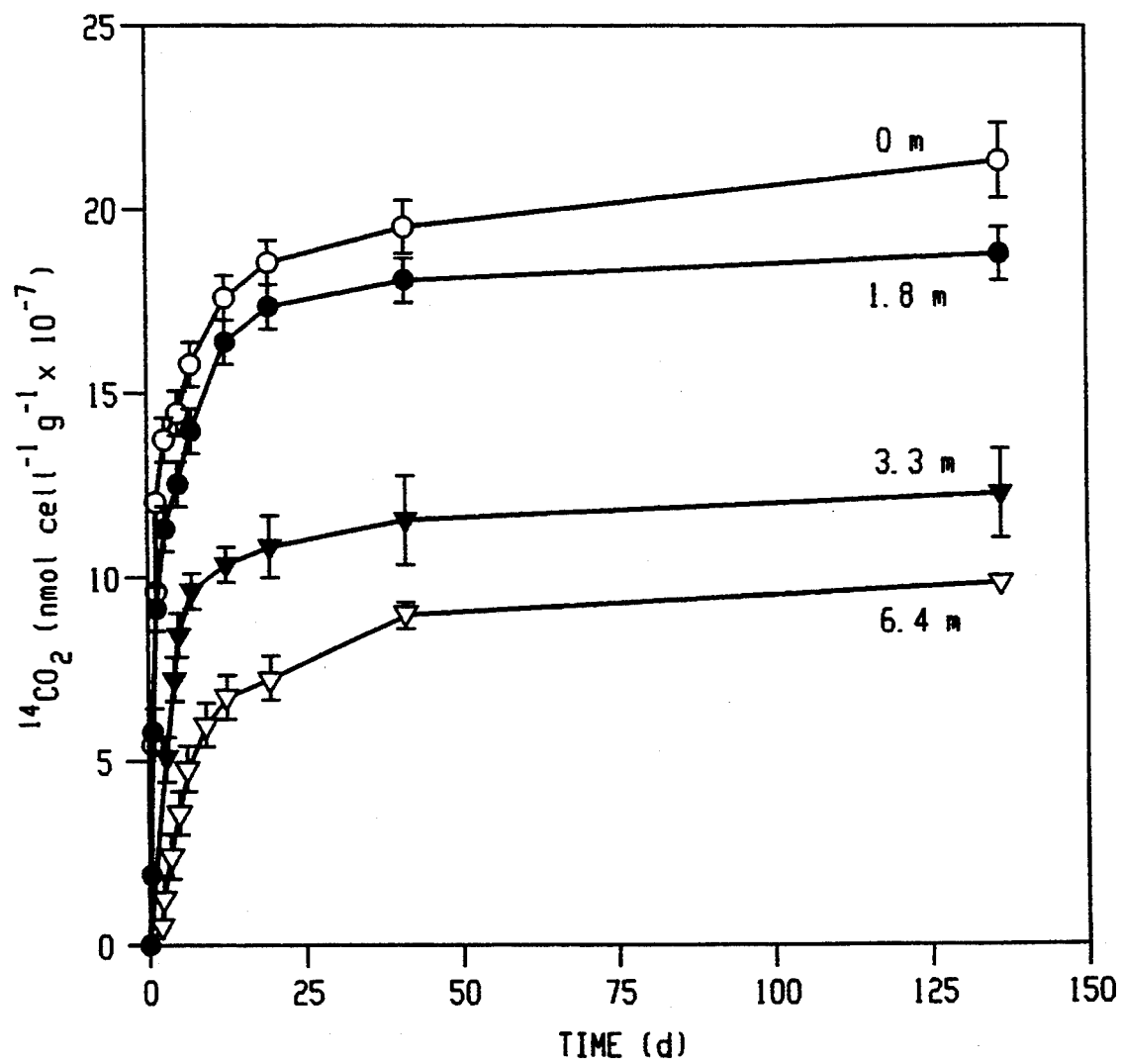
FIG. 14A. is a graph showing the mineralization of U-$^{14}$C-ring-atrazine in subsurface sediments inoculated with M91-3. The sediments were incubated at 25° C. without prior sterilization.
Figure 14B:
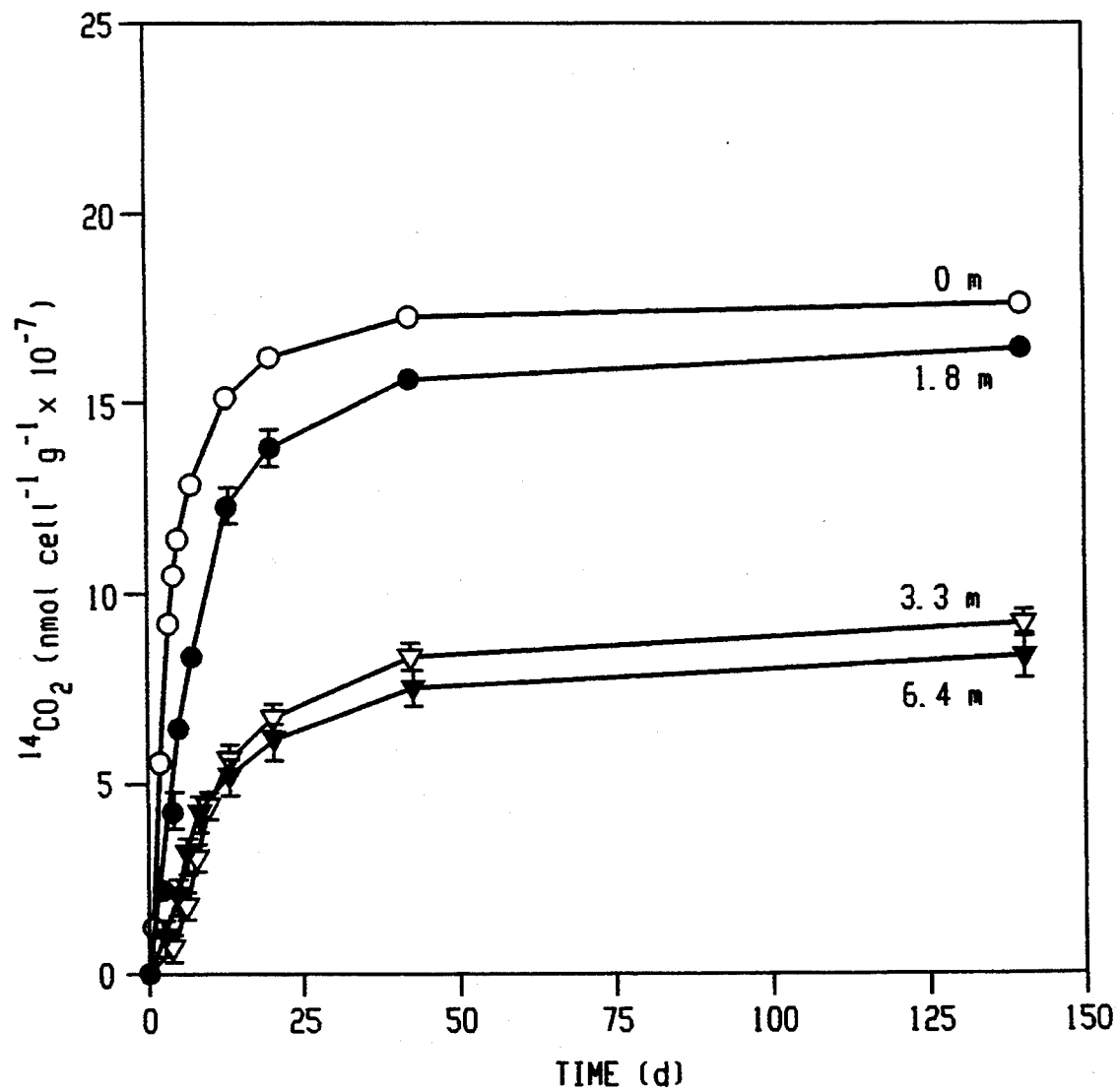
FIG. 14B. is a graph showing the mineralization of U-$^{14}$C-ring-atrazine in subsurface sediments inoculated with M91-3. The sediments were inoculated with $4.5 \times 10^7$ cells $g^{-1}$ and incubated at 25° C. with prior sterilization. The data points are means of samples taken from duplicate biometers and the error bars represent one standard deviation.
Figure 15A:
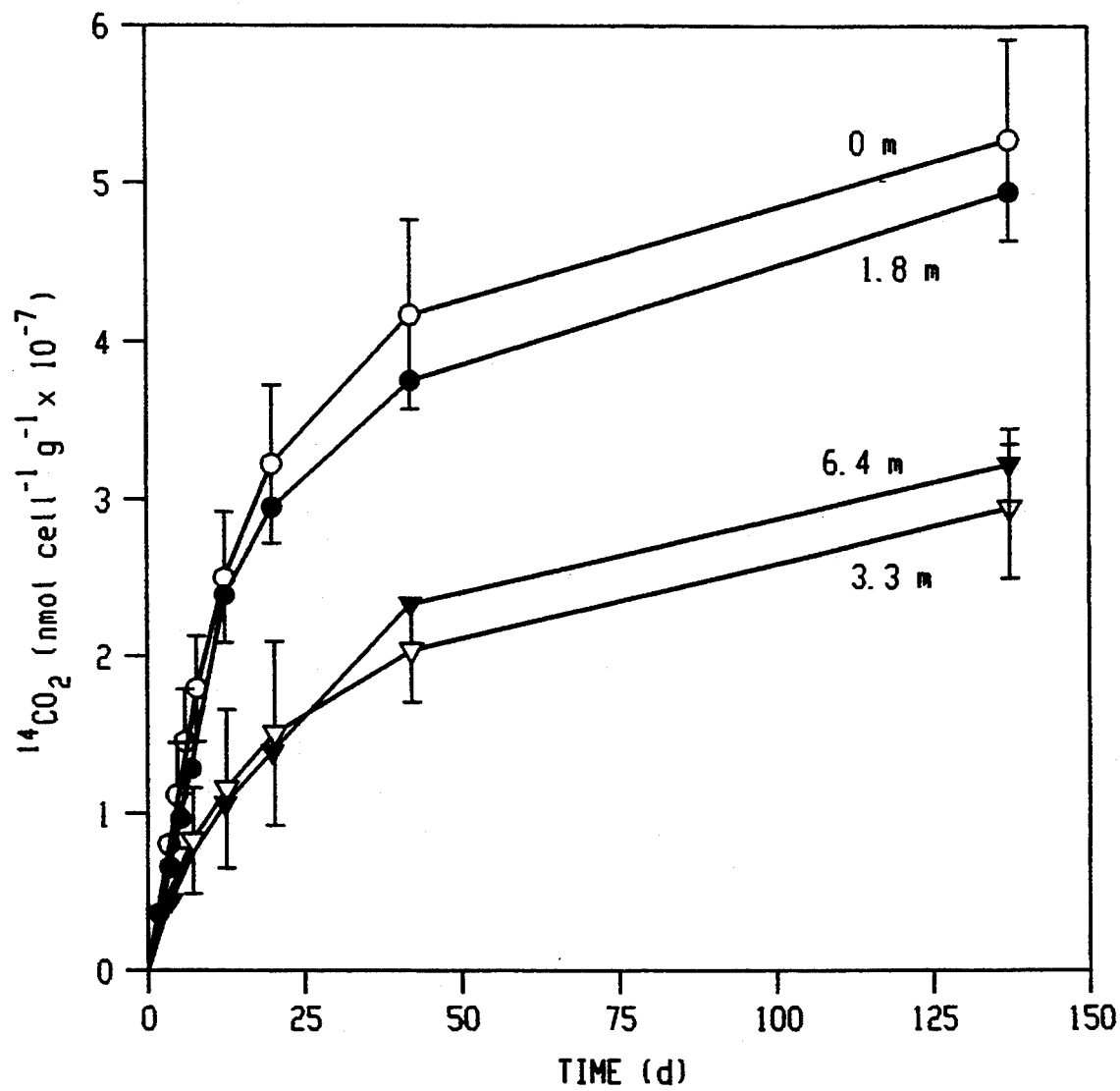
FIG. 15A. is a graph showing the mineralization of 2-$^{14}$C-ethyl-atrazine in subsurface sediments inoculated with M91-3. The sediments were incubated at 25° C. without prior sterilization.
Figure 15B:
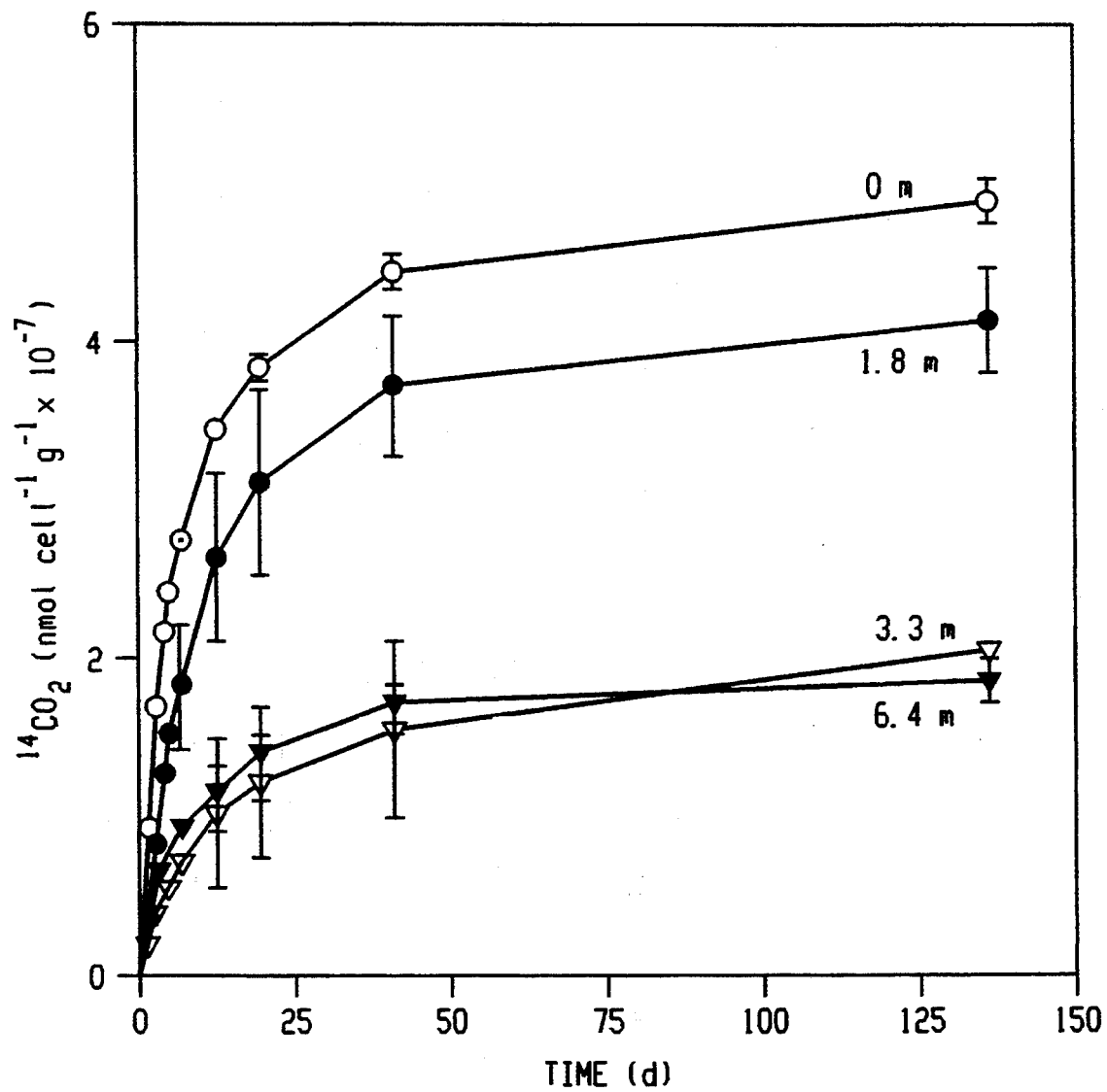
FIG. 15B. is a graph showing the mineralization of 2-$^{14}$C-ethyl-atrazine in subsurface sediments inoculated with the test culture. The sediments were incubated at 25° C. with prior sterilization. The data points are means of samples taken from duplicate biometers and the error bars represent one standard deviation.

Mineralization rates were modeled using a first-order $CO_2$ production equation in which the rate constant was the only adjustable parameter. The fitted rate constants are summarized for all treatments in Table IV. Representative mineralization curves have prepared for samples of inoculated soil and sediments collected at four depths ranging from the surface to 6.4 m are presented in FIGS. 14 and 15.

TABLE IV

Rate Constants of M91-3 from Mineralization of Atrazine in Sterile & Non-sterile Soil.

| Mean Sample Depth(m) | Unsterilized Ring, 25° C. | | | Unsterilized Ring, 10° C. | | |
|---|---|---|---|---|---|---|
| | k(d$^{-1}$) | Half-Life (d) | $r^2$ | k(d$^{-1}$) | Half-Life (d) | $r^2$ |
| 1.8 | 0.2136 | 3 | 0.99 | 0.0475 | 15 | 0.99 |
| 3.3 | 0.1034 | 7 | 0.97 | 0.0305 | 23 | 0.96 |
| 6.4 | 0.2736 | 3 | 0.95 | 0.0792 | 9 | 0.96 |
| 9.4 | 0.0936 | 7 | 0.99 | 0.0226 | 31 | 0.98 |
| 3.7 | 0.1099 | 6 | 0.96 | 0.0432 | 16 | 0.96 |
| 5.5 | 0.1152 | 6 | 0.96 | 0.0271 | 26 | 0.93 |
| 7.6 | 0.1426 | 5 | 0.97 | 0.0247 | 28 | 0.89 |
| Mean Sample Depth(m) | Unsterilized Chain, 25° C. | | | Unsterilized Chain, 10° C. | | |
| | k(d$^{-1}$) | Half-Life (d) | $r^2$ | k(d$^{-1}$) | Half-Life (d) | $r^2$ |
| 1.8 | 0.0442 | 16 | 0.99 | 0.0210 | 33 | 0.99 |
| 3.3 | 0.0331 | 21 | 0.94 | 0.0153 | 45 | 0.97 |
| 6.4 | 0.0324 | 21 | 0.97 | 0.0188 | 37 | 0.96 |
| 9.4 | 0.0282 | 25 | 0.99 | 0.0130 | 53 | 0.94 |

TABLE IV-continued

Rate Constants of M91-3 from Mineralization of Atrazine in Sterile & Non-sterile Soil.

| | | | | | | |
|---|---|---|---|---|---|---|
| 3.7 | 0.0245 | 28 | 0.98 | 0.0140 | 50 | 0.98 |
| 5.5 | 0.0252 | 28 | 0.96 | 0.0168 | 41 | 0.98 |
| 7.6 | 0.0252 | 28 | 0.99 | 0.0181 | 38 | 0.96 |

| Mean Sample | Pre-Sterilized Ring, 25° C. | | | Pre-Sterilized Ring, 10° C. | | |
|---|---|---|---|---|---|---|
| Depth(m) | $k(d^{-1})$ | Half-Life (d) | $r^2$ | $k(d^{-1})$ | Half-Life (d) | $r^2$ |
| 1.8 | 0.1008 | 7 | 1.00 | 0.0177 | 39 | 0.95 |
| 3.3 | 0.0648 | 11 | 0.98 | 0.0167 | 41 | 0.97 |
| 6.4 | 0.0888 | 8 | 0.97 | 0.0169 | 41 | 0.97 |
| 9.4 | 0.0499 | 14 | 0.95 | 0.0122 | 57 | 0.88 |
| 3.7 | 0.0566 | 12 | 0.98 | 0.0146 | 47 | 0.97 |
| 5.5 | 0.0576 | 12 | 0.99 | 0.0134 | 52 | 0.94 |
| 7.6 | 0.0624 | 11 | 0.97 | 0.0158 | 44 | 0.97 |

| Mean Sample | Pre-Sterilized Chain, 25° C. | | | Pre-Sterilized Chain, 10° C. | | |
|---|---|---|---|---|---|---|
| Depth(m) | $k(d^{-1})$ | Half-Life (d) | $r^2$ | $k(d^{-1})$ | Half-Life (d) | $r^2$ |
| 1.8 | 0.0806 | 9 | 0.96 | 0.0205 | 34 | 0.94 |
| 3.3 | 0.0713 | 10 | 0.99 | 0.0256 | 27 | 0.96 |
| 6.4 | 0.0977 | 7 | 0.94 | 0.0388 | 18 | 0.97 |
| 9.4 | 0.0384 | 18 | 0.97 | 0.0158 | 44 | 0.89 |
| 3.7 | 0.0734 | 9 | 0.98 | 0.0226 | 31 | 0.98 |
| 5.5 | 0.0631 | 11 | 0.99 | 0.0250 | 28 | 0.96 |
| 7.6 | 0.0523 | 13 | 0.99 | 0.0250 | 28 | 0.97 |

The mineralization of atrazine was negligible in uninoculated sediments. The mineralization by M91-3 varied with respect to both the extent and rate of $^{14}CO_2$ evolution depending upon sediment depths, incubation temperature, sterilization, and depending on whether the label was in the atrazine ring or in the ethyl side chain.

Determination of Sorption Parameters

Atrazine sorption to sediments was determined using a standard batch equilibration technique. Aqueous atrazine solutions containing 0, 0.05, 0.1, 0.5, 1, 3, and 5 mg $L^{-1}$ were prepared in 1 mM $CaCl_2$. Sediment samples were sieved without prior drying through a 2 mm sieve. Moist samples having a 5 g dry weight were placed in centrifuge tubes and 30 mL of a given atrazine solution was added. The suspensions were placed on a reciprocal shaker and incubated at 25° C. for 48 hours. After equilibration, the suspensions were centrifuged and the concentration of atrazine in the supernatant determined by HPLC. Sorption data were fitted to the Freundilch equation $$C_s = K_f C_{eq}^n$$

where $C_s$ is the amount sorbed (mg $Kg^{-1}$), $K_f$ is a measure of the degree of sorption ($LKg^{-1}$), $C_{eq}$ is the equilibrium solution concentration (mg $L^{-1}$), and n indicates the degree of nonlinearity between solution concentration and the amount sorbed. The sorption parameters were used to calculate equilibrium solution atrazine concentrations present in the biometers after adjustment for the difference in solid to solution ratio.

Atrazine sorption to subsurface sediments was independent of sample depth and was described by the Freundilch equation. Values of $K_f$ ranged from a high of 6.88 in the sediment collected from 9.4 m to a low of 0.81 at a depth of 6.4 meters. The degree of nonlinearity (n) varied from 0.97 in the 1.8 meter sediments to 0.78 in the 15.5 meter sediments.

The range in the degree of sorption in these sediments suggested variations in the initial solution concentration of atrazine. Therefore, it is reasonable to expect increased sorption to reduce the solution phase atrazine concentration, thereby limiting its bioavailability and mineralization rate in biodegradation experiments.

First-order mineralization rate constants were plotted as a function of the calculated equilibrium atrazine concentrations in the sediments at the initiation of the mineralization experiments. The results are depicted in FIGS. 16-19. Since the sorption and biometer measurements were made in different experimental systems, actual solution atrazine concentrations at the start of the experiment may differ considerably from the calculated values. However, relative differences in sorption appeared to explain some of the variation in mineralization rates, particularly for the sediments incubated at 25° C.

The mineralization of both ring-labeled and chain-labeled atrazine in uninoculated subsurface sediments was negligible. These findings suggest half-lives of several years for triazines in vadose zone and subsurface sediments. When the sediments were inoculated with the M91-3, both the chain-labeled atrazine and ring-labeled atrazine were rapidly mineralized. The data suggested that the primary restriction of the degradation of atrazine to the subsurface soil is due to a lack of an active degrading population rather than chemical or physical limitations such as sorption.

When the M91-3 was present and active, sorption to soil or sediments appeared to be rate-limiting at high mineralization rates, at the higher incubation temperature. At lower temperatures the effects of sorption became less significant.

Mineralization of Ring-labeled Atrazine in Inoculated Sediments

Figure 16:
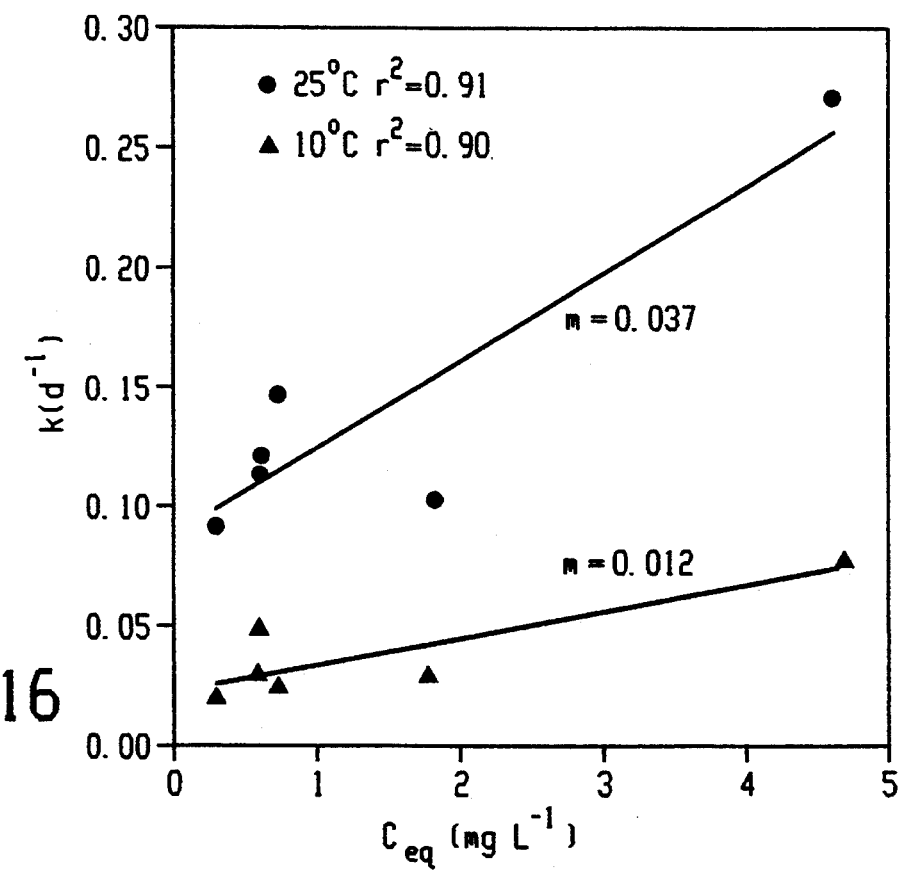
FIG. 16. is a graph showing the relationship between mineralization rate constant and equilibrium concentration of atrazine in a nonsterilized soil sample incubated with U-$^{14}$C-ring-atrazine.
Figure 17:
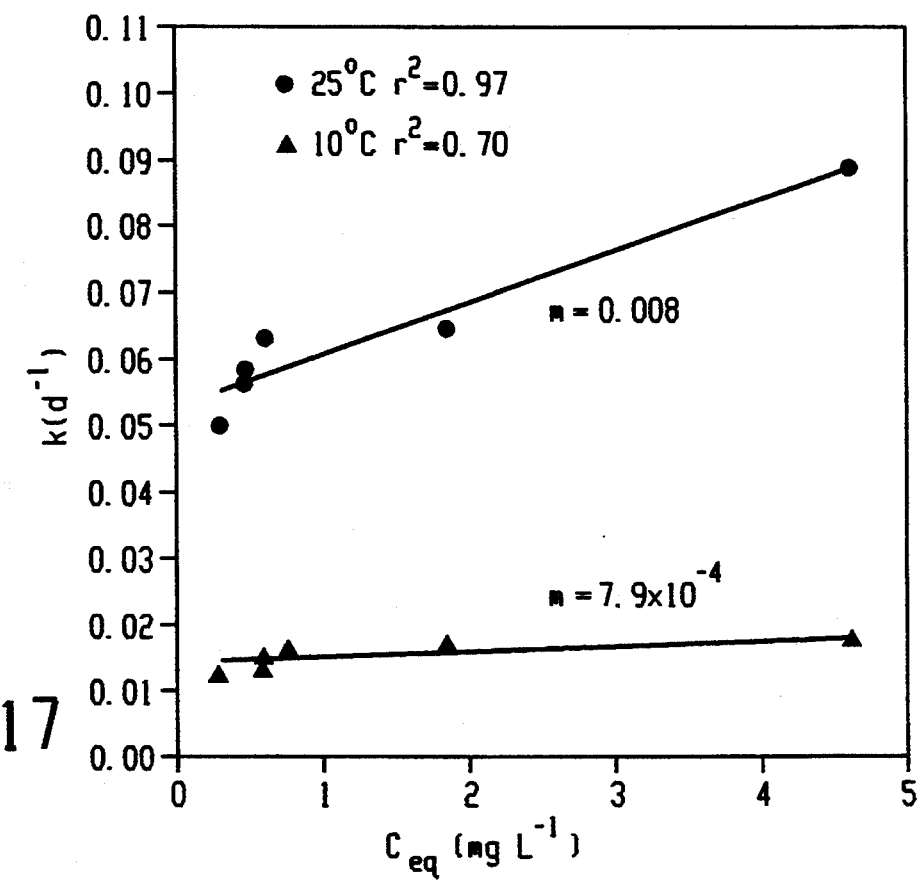
FIG. 17. is a graph showing the relationship between mineralization rate constant and equilibrium concentration of atrazine in samples incubated with U-$^{14}$C-ring-atrazine. The sediments were first sterilized and then inoculated with M91-3.

FIG. 16 shows the relationship between first-order mineralization rate constant (k) of ring labeled atrazine and the calculated solution equilibrium atrazine concentration ($C_{eq}$) in inoculated sediments without prior sterilization at 25° and 10° C. These data indicate that a reduction in $C_{eq}$ due to atrazine sorption influences the mineralization rates when an active atrazine degrading bacterial population is present. The effect of sorption was less significant in the sediments incubated at 10° C. These data suggest that the mineralization rate of atrazine was limited by temperature rather than by sorption. The difference in sorption effects between the two incubation temperatures was more pronounced in sediments that were sterilized prior to inoculation. The extent and rate of mineralization of atrazine was greater in non-sterilized sediments, suggesting that the indigenous microbial population in the sediment sample also contributed to the overall release of $^{14}CO_2$ from ring-labeled atrazine.

Mineralization of Chain-Labeled Atrazine in Inoculated Sediments

Figure 18:
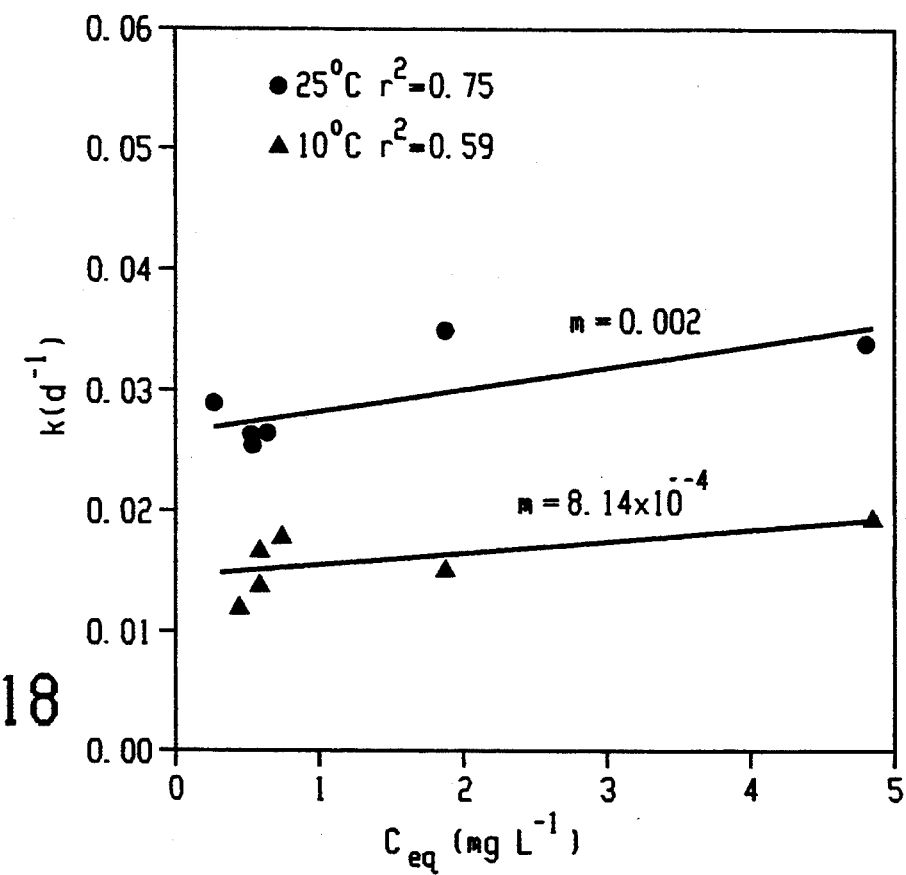
FIG. 18. is a graph showing the relationship between mineralization rate constant and equilibrium concentration of atrazine in nonsterilized soil samples incubated with 2-$^{14}$C-ethyl-atrazine.
Figure 19:
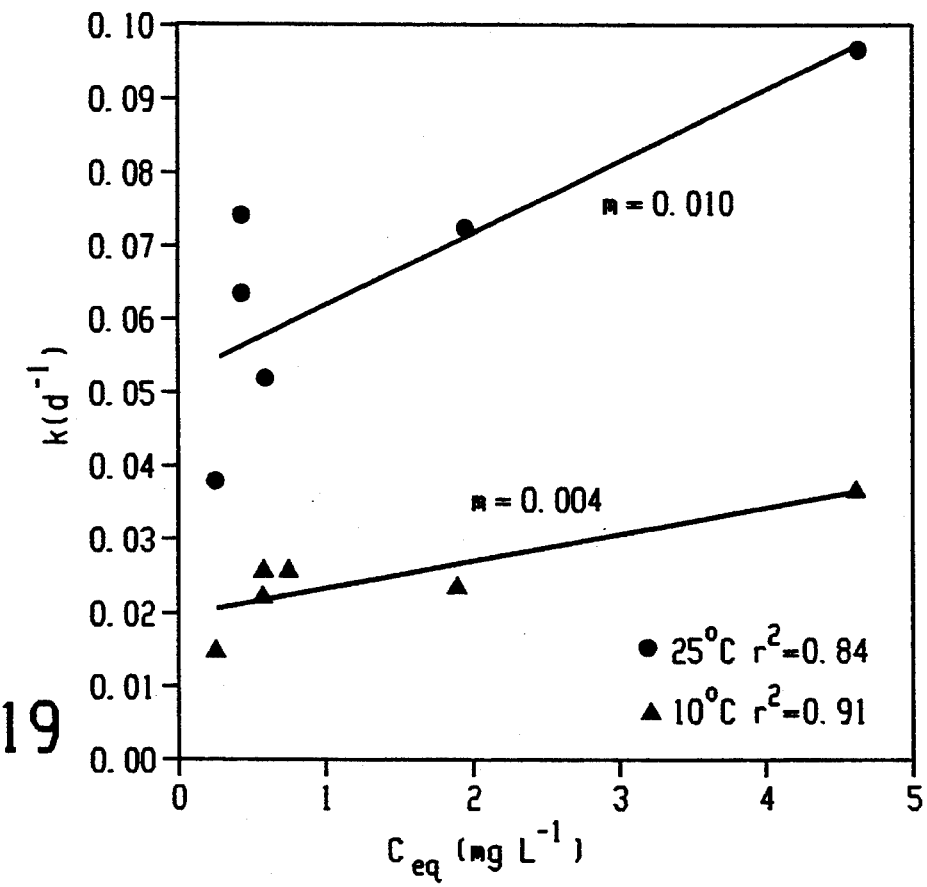
FIG. 19. is a graph showing the relationship between mineralization rate constant and equilibrium concentration of atrazine in samples incubated with 2-$^{14}$C-ethyl-atrazine. The sediments were first sterilized and then inoculated with M91-3.

The overall release of $^{14}CO_2$ from (2-$^{14}$C-ethyl)-atrazine was less than that observed for sediments treated with ring-labeled atrazine. Presumably this is a result of the assimilation of the labeled side-chain carbon either by the M91-3 or by the indigenous microbial population in nonsterilized soil. The effects of sorption were more pronounced in sediments that were sterilized prior to inoculation as shown in FIG. 18 and 19.

No $^{14}CO_2$ evolved from soil or sediments without the addition of the M91-3, except the surface soil samples collected at 0 to 7.5 cm, where only about 14% of the added label evolved after 45 days. The results indicate that the major limitation to atrazine biodegradation in the sediments beneath this site is the absence of an atrazine degrading population rather than nutrient deficits or sorption.

The inoculum of M91-3 may be applied to samples containing s-triazines such as soil or sediments, or water such as wastewater, in a variety of ways including for example, in liquid form such as culture media, or a solid form.

It is understood that this description is made only by way of example, that the invention is not limited to the particular embodiments described herein, and that the various rearrangements, modifications, and substitutions may be implemented without departing from the true spirit of the invention hereinafter claimed.

What is claimed is:

1. A biologically pure culture of a bacterial strain capable of degrading atrazine to carbon dioxide, biuret, urea and ammonia, having all of the identifying characteristics of strain M91-3, ATCC 55551.

* * * * *